(12) United States Patent
Ingham et al.

(10) Patent No.: US 7,504,209 B2
(45) Date of Patent: Mar. 17, 2009

(54) METHOD AND DEVICE FOR INTEGRATED NUCLEIC ACID INTEGRITY ASSESSMENT AND ANALYSIS

(75) Inventors: Colin John Ingham, Den Bosch (NL); Richard Michael Anthony, Amsterdam (NL)

(73) Assignee: PamGene B.V., Den Bosch (NL)

( * ) Notice: Subject to any disclaimer, the term of this patent is extended or adjusted under 35 U.S.C. 154(b) by 97 days.

(21) Appl. No.: 10/547,577

(22) PCT Filed: Mar. 1, 2004

(86) PCT No.: PCT/EP2004/002025

§ 371 (c)(1),
(2), (4) Date: Nov. 1, 2006

(87) PCT Pub. No.: WO2004/079005

PCT Pub. Date: Sep. 16, 2004

(65) Prior Publication Data

US 2007/0259340 A1 Nov. 8, 2007

Related U.S. Application Data

(60) Provisional application No. 60/472,155, filed on May 21, 2003.

(30) Foreign Application Priority Data

| Mar. 4, 2003 | (EP) | ................................. 03447045 |
| Nov. 6, 2003 | (EP) | ................................. 03025294 |

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3
(58) Field of Classification Search .................... 435/6; 536/23.1, 24.3
See application file for complete search history.

(56) References Cited

U.S. PATENT DOCUMENTS

| 5,543,499 | A | * | 8/1996 | Brewer ........................ 530/350 |
| 7,011,947 | B2 | * | 3/2006 | Golub et al. ................... 435/6 |
| 7,138,569 | B2 | * | 11/2006 | Collmer et al. ............. 800/301 |
| 7,332,590 | B2 | * | 2/2008 | Nacht et al. ................. 536/23.1 |
| 2003/0082596 | A1 | * | 5/2003 | Mittmann ....................... 435/6 |
| 2003/0087265 | A1 | * | 5/2003 | Sauter et al. ................... 435/6 |
| 2006/0234242 | A1 | * | 10/2006 | Cheatham et al. ............. 435/6 |
| 2007/0259340 | A1 | * | 11/2007 | Schramm ....................... 435/6 |

FOREIGN PATENT DOCUMENTS

| WO | WO 02/052038 A | 7/2002 |
| WO | WO 02/099064 A | 12/2002 |

OTHER PUBLICATIONS

Salowsky et al., "High Sensitivity Quality Control of RNA Samples Using RNA 6000 Pico LabChip Kit." Aglient Technologies Application, pp. 1-8, Dec. 1, 2002.
GEO Database Accession No. GPL96 GPL96, "Affymetrix GeneChip Human Genome U133 Array Set HG-U133A," as retrieved on Apr. 3, 2005 from http://www.ncbi.nih.gov/, published on Nov. 3, 2002.

* cited by examiner

*Primary Examiner*—Ethan Whisenant
(74) *Attorney, Agent, or Firm*—Amster, Rothstein & Ebenstein LLP

(57) ABSTRACT

The present invention relates to methods for integrated ribonucleic acid integrity assessment and analysis comprising the steps of: (a) providing a support having immobilized thereon a set of detector probes and a set of at least two control probes, wherein (i) a first of said at least two control probes is complementary to 23S or 28S rRNA or a functionally equivalent RNA, and (ii) a second of said at least two control probes is complementary to 16S or 18S10 rRNA or a functionally equivalent RNA; (b) contacting said support with analyte ribonucleic acids derived from a sample, under conditions allowing hybridisation of complementary analyte ribonucleic acids and immobilized probes to form analyte ribonucleic acid/probe complexes; wherein said hybridisation generates a detectable signal; 15 (c) detecting signals generated by said complexes; (d) determining the ratio of signals generated by the 28S/control probe and 18S rRNA/control probe or 23S rRNA/control probe and 16S rRNA/control probe or functionally equivalent rRNA/control probe complexes; (e) assessing the integrity of said sample; and 20 (f) evaluating microarray analysis results in view of said integrity assessment. The present invention further relates to use of said methods as well as microarrays, devices comprising said microarrays, kits for carrying out said methods and computer products.

20 Claims, 3 Drawing Sheets

Figure 1:
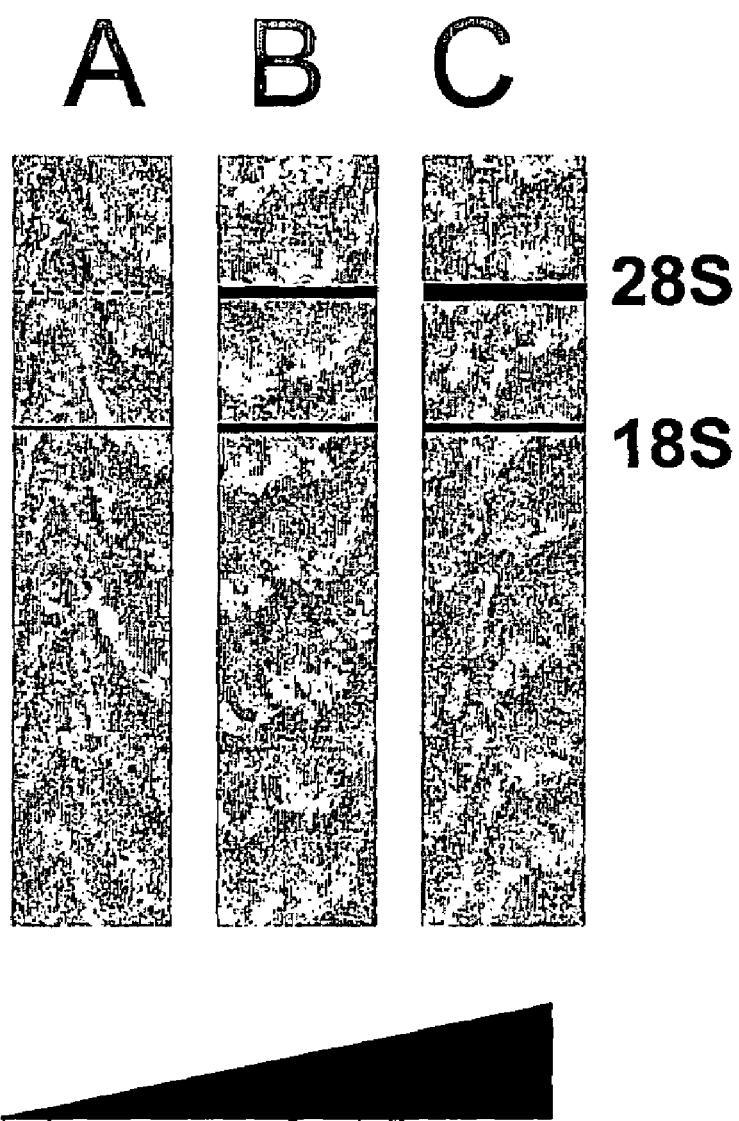

SEQUENCE LISTING

<160> NUMBER OF SEQ ID NOS: 38

<210> SEQ ID NO 1
<211> LENGTH: 20

```
<212> TYPE: DNA
<213> ORGANISM: Artificial Sequence
<220> FEATURE:
<223> OTHER INFORMATION: Promotor

<400> SEQUENCE: 1
taatacgact cactataggg                                                        0

<210> SEQ ID NO 2
<211> LENGTH: 20
<212> TYPE: DNA
<213> ORGANISM: Artificial Sequence
<220> FEATURE:
<223> OTHER INFORMATION: Promotor

<400> SEQUENCE: 2
taatacgact cactataggg                                                       20

<210> SEQ ID NO 3
<211> LENGTH: 20
<212> TYPE: DNA
<213> ORGANISM: Artificial Sequence
<220> FEATURE:
<223> OTHER INFORMATION: Promotor

<400> SEQUENCE: 3
taatacgact cactataggg                                                       20

<210> SEQ ID NO 4
<211> LENGTH: 20
<212> TYPE: DNA
<213> ORGANISM: Artificial Sequence
<220> FEATURE:
<223> OTHER INFORMATION: Promotor

<400> SEQUENCE: 4
taatacgact cactataggg                                                       20

<210> SEQ ID NO 5
<211> LENGTH: 20
<212> TYPE: DNA
<213> ORGANISM: Artificial Sequence
<220> FEATURE:
<223> OTHER INFORMATION: Promotor

<400> SEQUENCE: 5
taatacgact cactataggg                                                       20

<210> SEQ ID NO 6
<211> LENGTH: 20
<212> TYPE: DNA
<213> ORGANISM: Artificial Sequence
<220> FEATURE:
<223> OTHER INFORMATION: Promotor

<400> SEQUENCE: 6
taatacgact cactataggg                                                       20

<210> SEQ ID NO 7
<211> LENGTH: 43
<212> TYPE: DNA
<213> ORGANISM: Artificial Sequence
<220> FEATURE:
<223> OTHER INFORMATION: Primer

<400> SEQUENCE: 7
```

```
taatacgact cactataggg ttacacgccg ctcggtggag aag          43

<210> SEQ ID NO 8
<211> LENGTH: 46
<212> TYPE: DNA
<213> ORGANISM: Artificial Sequence
<220> FEATURE:
<223> OTHER INFORMATION: Primer

<400> SEQUENCE: 8
taatacgact cactataggg atagtcaagt tcgaccgtct tctcag       46

<210> SEQ ID NO 9
<211> LENGTH: 45
<212> TYPE: DNA
<213> ORGANISM: Artificial Sequence
<220> FEATURE:
<223> OTHER INFORMATION: Primer

<400> SEQUENCE: 9
taatacgact cactatagga tagtcaagtt cgaccgtctt ctcag        45

<210> SEQ ID NO 10
<211> LENGTH: 44
<212> TYPE: DNA
<213> ORGANISM: Artificial Sequence
<220> FEATURE:
<223> OTHER INFORMATION: Primer

<400> SEQUENCE: 10
taatacgact cactatagat agtcaagttc gaccgtcttc tcag         44

<210> SEQ ID NO 11
<211> LENGTH: 60
<212> TYPE: DNA
<213> ORGANISM: Artificial Sequence
<220> FEATURE:
<223> OTHER INFORMATION: Probe

<400> SEQUENCE: 11
tacctggttg atcctgccag tagcatatgc ttgtctcaaa gattaagcca tgcatgtcta   60

<210> SEQ ID NO 12
<211> LENGTH: 60
<212> TYPE: DNA
<213> ORGANISM: Artificial Sequence
<220> FEATURE:
<223> OTHER INFORMATION: Probe

<400> SEQUENCE: 12
atcctgccag tagcatatgc ttgtctcaaa gattaagcca tgcatgtcta agtacgcacg   60

<210> SEQ ID NO 13
<211> LENGTH: 59
<212> TYPE: DNA
<213> ORGANISM: Artificial Sequence
<220> FEATURE:
<223> OTHER INFORMATION: Probe

<400> SEQUENCE: 13
gtacagtgaa actgcgaatg gctcattaaa tcagttatgg ttcctttggt cgctcgctc    59

<210> SEQ ID NO 14
<211> LENGTH: 59
<212> TYPE: DNA
<213> ORGANISM: Artificial Sequence
```

```
<220> FEATURE:
<223> OTHER INFORMATION: Probe

<400> SEQUENCE: 14
ggataactgt ggtaattcta gagctaatac atgccgacgg gcgctgaccc ccttcgcgg      59

<210> SEQ ID NO 15
<211> LENGTH: 59
<212> TYPE: DNA
<213> ORGANISM: Artificial Sequence
<220> FEATURE:
<223> OTHER INFORMATION: Probe

<400> SEQUENCE: 15
gacgacccat tcgaacgtct gccctatcaa ctttcgatgg tagtcgccgt gcctaccat      59

<210> SEQ ID NO 16
<211> LENGTH: 59
<212> TYPE: DNA
<213> ORGANISM: Artificial Sequence
<220> FEATURE:
<223> OTHER INFORMATION: Probe

<400> SEQUENCE: 16
gaatcagggt tcgattccgg agagggagcc tgagaaacgg ctaccacatc caaggaagg      59

<210> SEQ ID NO 17
<211> LENGTH: 59
<212> TYPE: DNA
<213> ORGANISM: Artificial Sequence
<220> FEATURE:
<223> OTHER INFORMATION: Probe

<400> SEQUENCE: 17
ctttcgaggc cctgtaattg gaatgagtcc actttaaatc ctttaacgag gatccattg      59

<210> SEQ ID NO 18
<211> LENGTH: 59
<212> TYPE: DNA
<213> ORGANISM: Artificial Sequence
<220> FEATURE:
<223> OTHER INFORMATION: Probe

<400> SEQUENCE: 18
gagtgttcaa agcaggcccg agccgcctgg ataccgcagc taggaataat ggaatagga      59

<210> SEQ ID NO 19
<211> LENGTH: 60
<212> TYPE: DNA
<213> ORGANISM: Artificial Sequence
<220> FEATURE:
<223> OTHER INFORMATION: Probe

<400> SEQUENCE: 19
gaattcacca agcgttggat tgttcaccca ctaatagggA acgtgagctg ggtttagacc      60

<210> SEQ ID NO 20
<211> LENGTH: 60
<212> TYPE: DNA
<213> ORGANISM: Artificial Sequence
<220> FEATURE:
<223> OTHER INFORMATION: Probe

<400> SEQUENCE: 20
agcgttggat tgttcaccca ctaatagggA acgtgagctg ggtttagacc gtcgtgagac      60
```

<210> SEQ ID NO 21
<211> LENGTH: 59
<212> TYPE: DNA
<213> ORGANISM: Artificial Sequence
<220> FEATURE:
<223> OTHER INFORMATION: Probe

<400> SEQUENCE: 21
gagctgggtt tagaccgtcg tgagacaggt tagttttacc ctactgatga tgtgttgtt      59

<210> SEQ ID NO 22
<211> LENGTH: 55
<212> TYPE: DNA
<213> ORGANISM: Artificial Sequence
<220> FEATURE:
<223> OTHER INFORMATION: Probe

<400> SEQUENCE: 22
ggtttagacc gtcgtgagac aggttagttt taccctactg atgatgtgtt gttgc          55

<210> SEQ ID NO 23
<211> LENGTH: 55
<212> TYPE: DNA
<213> ORGANISM: Artificial Sequence
<220> FEATURE:
<223> OTHER INFORMATION: Probe

<400> SEQUENCE: 23
ctcagtacga gaggaaccgc aggttcagac atttggtgta tgtgcttggc tgagg          55

<210> SEQ ID NO 24
<211> LENGTH: 59
<212> TYPE: DNA
<213> ORGANISM: Artificial Sequence
<220> FEATURE:
<223> OTHER INFORMATION: Probe

<400> SEQUENCE: 24
catctgtggg attatgactg aacgcctcta agtcagaatc ccgcccaggc gaacgatac      59

<210> SEQ ID NO 25
<211> LENGTH: 55
<212> TYPE: DNA
<213> ORGANISM: Artificial Sequence
<220> FEATURE:
<223> OTHER INFORMATION: Probe

<400> SEQUENCE: 25
gaacgtacca tctgtgggat tatgactgaa cgcctctaag tcagaatccc gccca          55

<210> SEQ ID NO 26
<211> LENGTH: 55
<212> TYPE: DNA
<213> ORGANISM: Artificial Sequence
<220> FEATURE:
<223> OTHER INFORMATION: Probe

<400> SEQUENCE: 26
cagctccctc gctgcgatct attgaaagtc agccctcgac acaagggttt gtccg          55

<210> SEQ ID NO 27
<211> LENGTH: 59
<212> TYPE: DNA
<213> ORGANISM: Artificial Sequence
<220> FEATURE:
<223> OTHER INFORMATION: Oligonucleotide -continued

```
<400> SEQUENCE: 27
gagcgagcga ccaaaggaac cataactgat ttaatgagcc attcgcagtt tcactgtac        59

<210> SEQ ID NO 28
<211> LENGTH: 59
<212> TYPE: DNA
<213> ORGANISM: Artificial Sequence
<220> FEATURE:
<223> OTHER INFORMATION: Oligonucleotide

<400> SEQUENCE: 28
atggtaggca cggcgactac catcgaaagt tgatagggca gacgttcgaa tgggtcgtc        59

<210> SEQ ID NO 29
<211> LENGTH: 59
<212> TYPE: DNA
<213> ORGANISM: Artificial Sequence
<220> FEATURE:
<223> OTHER INFORMATION: Oligonucleotide

<400> SEQUENCE: 29
tcctattcca ttattcctag ctgcggtatc caggcggctc gggcctgctt tgaacactc        59

<210> SEQ ID NO 30
<211> LENGTH: 60
<212> TYPE: DNA
<213> ORGANISM: Artificial Sequence
<220> FEATURE:
<223> OTHER INFORMATION: Oligonucleotide

<400> SEQUENCE: 30
ggtctaaacc cagctcacgt tccctattag tgggtgaaca atccaacgct tggtgaattc       60

<210> SEQ ID NO 31
<211> LENGTH: 59
<212> TYPE: DNA
<213> ORGANISM: Artificial Sequence
<220> FEATURE:
<223> OTHER INFORMATION: Oligonucleotide

<400> SEQUENCE: 31
aacaacacat catcagtagg gtaaaactaa cctgtctcac gacggtctaa acccagctc        59

<210> SEQ ID NO 32
<211> LENGTH: 55
<212> TYPE: DNA
<213> ORGANISM: Artificial Sequence
<220> FEATURE:
<223> OTHER INFORMATION: Oligonucleotide

<400> SEQUENCE: 32
cctcagccaa gcacatacac caaatgtctg aacctgcggt tcctctcgta ctgag            55

<210> SEQ ID NO 33
<211> LENGTH: 55
<212> TYPE: DNA
<213> ORGANISM: Artificial Sequence
<220> FEATURE:
<223> OTHER INFORMATION: Oligonucleotide

<400> SEQUENCE: 33
cggacaaacc cttgtgtcga gggctgactt tcaatagatc gcagcgaggg agctg            55

<210> SEQ ID NO 34
```

-continued

```
<211> LENGTH: 23
<212> TYPE: DNA
<213> ORGANISM: Artificial Sequence
<220> FEATURE:
<223> OTHER INFORMATION: Probe

<400> SEQUENCE: 34
aatgatcctt ccgcaggttc acc                                            23

<210> SEQ ID NO 35
<211> LENGTH: 27
<212> TYPE: DNA
<213> ORGANISM: Artificial Sequence
<220> FEATURE:
<223> OTHER INFORMATION: Probe

<400> SEQUENCE: 35
gatagtcaag ttcgaccgtc ttctcag                                        27

<210> SEQ ID NO 36
<211> LENGTH: 25
<212> TYPE: DNA
<213> ORGANISM: Artificial Sequence
<220> FEATURE:
<223> OTHER INFORMATION: Probe

<400> SEQUENCE: 36
tttgagacaa gcatatgcta ctggc                                          25

<210> SEQ ID NO 37
<211> LENGTH: 23
<212> TYPE: DNA
<213> ORGANISM: Artificial Sequence
<220> FEATURE:
<223> OTHER INFORMATION: Probe

<400> SEQUENCE: 37
ttacacgccg ctcggtggag aag                                            23

<210> SEQ ID NO 38
<211> LENGTH: 25
<212> TYPE: DNA
<213> ORGANISM: Artificial Sequence
<220> FEATURE:
<223> OTHER INFORMATION: Probe

<400> SEQUENCE: 38
tccctattag tgggtgaaca atcca                                          25
```

METHOD AND DEVICE FOR INTEGRATED NUCLEIC ACID INTEGRITY ASSESSMENT AND ANALYSIS

This is a U.S. national phase of PCT Application No. PCT/EP2004/002025, filed Mar. 1, 2004, and claims priority to European Application No. 03447045.0, filed Mar. 4, 2003, U.S. application Ser. No. 60/472,155, filed May 21, 2003 and European Application No. 03025294.4, filed Nov. 6, 2003.

FIELD OF THE INVENTION

The present invention relates to the field of hybridisation arrays. More specifically, the present invention concerns a method for assessment of RNA integrity in microarray analysis of biological samples. This novel method relies on the use of a combined array comprising a set of at least two immobilized control oligonucleotides wherein a first of said control probes is complementary to 23S or 28S or a functionally equivalent rRNA, and wherein a second control probe is complementary to 16S or 18S or a functionally equivalent rRNA, as well as detector probes complementary to mRNA-derived amplicons.

BACKGROUND

Assessment of RNA integrity as sample quality control is critical for good microarray performance and analysis. RNA degradation is common, for example in samples from tissue biopsies where there is often considerable delay during surgery before appropriate storage. In RNA integrity quality control, commonly the ratio of the two major ribosomal RNAs (rRNA) is used to indicate general RNA integrity quality (typically 18S and 28S in eukaryotes, 16S and 23S in prokaryotes). These are abundant transcripts (over half the total cellular RNA) and easily resolved by agarose gel or microfluidic systems. Typically a 2:1 ratio in the total amount of the 28S rRNA compared to the 18S rRNA indicates a high integrity sample.

Typical disadvantages of pre-analysis RNA quality control by e.g. gel electrophoresis are the requirement of high amounts of total RNA (approximately 1 µg) and often the requirement of a substantial amount of the sample to be expended in this assessment.

In current practices, however, a growing requirement is to assess RNA quality in small (picogram to nanogram) samples—for example those obtained from laser capture micro dissection and often, current methods requiring the entire sample or more to be expended in pre-analysis quality control are therefore not appropriate.

Efforts to reduce the amount of total RNA for quality assessment have been numerous including RT-PCR of the 18S rRNA using 25 ng or less starting material but this is a significant effort. Alternatively, hybridisation of primers to the 28S rRNA have been used as a predictor of RNA integrity in in situ hybridisations.

Further minimalisation of sample quantity was achieved by the introduction of Agilent's Lab-on-a-Chip technology which provides an alternative to traditional gel-based analysis that integrates the quantitation of RNA samples with quality assessment in a single assay; as little as 1 µl of 10 ng/µl is required per analysis.

The challenge to perform an integrated microarray analysis of RNA-derived samples, including sample analysis (e.g. expression profiling) as well as sample quality/integrity assessment, however, remains.

Various scenarios of microarray analysis quality control exist; employing an internal standard which may be exogenous or endogenous. Current quality control, however merely focuses on the normalization of the output results to compensate for differences in labelling and detection efficiencies and for differences in spotted nucleic acid quantity, surface anomalies and overall slide quality. RNA integrity in current microarray analysis is not addressed.

The feasibility of using rRNA as an endogenous standard in microarray analysis has been demonstrated in WO 02/05038 which discloses a method for providing an rRNA internal standard.

rRNAs as an internal endogenous standard is generally considered ideal in a large experimental field in view of its expression which does not vary during cell cycle, between cell types, or in response to the experimental treatments that one wishes to examine. However, for such an endogenous standard to be valid in nucleic acid microarray analysis it is crucial that it be of similar relative abundance as the target transcript. Since rRNA is found in massive amounts relative to other RNAs, any simultaneous method of detecting rRNAs at the same time as other RNA species must take this into account (e.g. by differential amplification) while remaining an accurate assessment of the original levels.

In WO 02/05038, the excess signal coming from the labelled rRNA (or from the cDNA generated from the rRNA) is competed out and the signal detected for it is reduced to a range compatible with that of the signal for the other labelled RNA's by the post-transcriptional addition of a quantity of an unlabelled ribosomal nucleic acid competitor probe into the hybridisation buffer to compete with the immobilized ribosomal capture probe. The use of such internal standard in test and reference samples then allows for the provision of a normalization factor which allows for the correction of the hybridisation signal resulting from the binding of target cDNA with corresponding capture probe. A problem with the above method is however that a lot of excess of fluorescently labelled amplified rRNA is present in the hybridisation mix, which contributes to high background signals.

In current practice, however no microarray hybridisation analysis with integrated RNA integrity control has yet been proved feasible. There is a need for the assessment of RNA integrity to be related to the performance of hybridisations of the amplified RNA (aRNA) to the array.

The present invention aims at providing a method to assess RNA integrity in microarray analysis assays for nucleic acid hybridisation. More in particular, the present invention aims at providing a method for microarray analysis of a nucleic acid sample wherein said sample is analysed for its original integrity in combination with its analysis towards a particular application; e.g. gene expression profiling. The method of the present invention thus aims at providing a nucleic acid analysis method with no requirement to expend any sample to a pre-analysis quality control.

SUMMARY OF THE INVENTION

Commonly, amplifications for array purposes use total RNA including rRNA. The first step in making aRNA is to extend an oligo dT primer annealed to the 3' poly A tract of messenger RNAs (mRNAs) to make the first strand cDNA. In the present invention additional sequence specific primers are being extended at the same time in the same reverse transcriptase reaction; i.e. In the present invention, amplification reactions are seeded with a set of at least two additional primers that specifically hybridises to the 18S and 28S rRNAs in addition to an oligo-dT primer. These primers allow synthesis of a labelled product that is used to assess rRNA abundance by hybridisation to the array.

Further, it is known that prokaryotic mRNA polyadenylates though the tracts of poly A tend to be shorter and not all mRNAs of a given species are polyadenylated. Whilst this may be connected with mRNA stability or even translation, the full significance of this remains, however, unclear (N. Sarkar, Annual Review of Biochemistry, 1997, Vol. 66, pp. 173-197). It is, however, perfectly possible to amplify the polyadenylated sub-population. Accordingly, the present invention is equally suitable for prokaryotic systems wherein amplification reactions are then seeded with a set of at least two additional primers that specifically hybridises to the 16S and 23S rRNAs in addition to an oligo-dT primer.

The present invention provides a method for integrated nucleic acid integrity assessment and analysis comprising employing a combined array of nucleic acid molecules immobilized on a solid support whereby said array of nucleic acid molecules comprises a combination of control complementary oligo's to the amplified RNA derived from 16S, 18S or a functionally equivalent rRNA and control complementary oligo's to the amplified rRNA derived from 23S, 28S or a functionally equivalent rRNA as well as detector probes complementary to mRNA.

The term "functionally equivalent rRNA" as used throughout the present specification refers to ribosomal nucleic acids having a slightly different size but exerting a same function. For example; in yeast the 26S rRNA is the functionally equivalent of the 28S rRNA in humans.

Still other rRNA species may exist in cells that may also be good indicators of RNA quality. These include 5S rRNA that is known from many human and prokaryotic species as well as plant species. The present invention contemplates the use of the said other rRNA species if these would be specifically primed concurrently with oligo dT priming of polyadenylated mRNA.

In addition, the present invention contemplates the use of non-polyadenylated RNA as targets for specific priming in view of the criteria that imply that (1) the RNA should be an indicator of sample quality and (2) the RNA should be present in a total RNA sample and (3) the RNA should not be polyadenylated such as some regulatory rRNAs, some histone mRNAs and some viral RNAs. In particular the latter criterion is critical in view of the fact that some RNA species may be present in polyadenylated and non-polyadenylated form Accordingly, the array as used in the present invention typically has one or more spots containing oligos complimentary to amplified 16S or 18S rRNA or a functionally equivalent rRNA; one or more spots containing oligos complimentary to amplified 23S or 28S rRNA or a functionally equivalent rRNA and one or more spots containing oligos complimentary to amplified mRNA.

In general each spot on the array has one oligonucleotide; i.e. one oligonucleotide species. Thus, the oligonucleotide molecules within one spot are usually as near to identical as limitations on synthesis allow. Alternatively, one spot may comprise more than one oligonucleotide species which may be complementary to e.g. different parts of the e.g. target 18S or 28S rRNA; for example some parts of an RNA molecule may be more sensitive to degradation than others. The use of such oligonucleotides allows the detection of partially degraded RNA's; this is not the case in methods known in the art such as agarose gel analysis or the Bioanalyzer technology by Agilent.

Accordingly, the present invention provides a method for integrated ribonucleic acid integrity assessment and analysis comprising the steps of:

(a) providing a support having thereon a set of immobilized detector probes and a set of at least two control probes, wherein
  (i) a first of said at least two control probes is complementary to 23S or 28S rRNA or a functionally equivalent rRNA, and
  (ii) a second of said at least two control probes is complementary to 16S or 18S rRNA or a functionally equivalent rRNA;
(b) contacting said support with analyte ribonucleic acids derived from a sample, under conditions allowing hybridisation of complementary analyte ribonucleic acids and immobilized probes to form analyte ribonucleic acid/probe complexes; wherein said hybridisation generates a detectable signal;
(c) detecting signals generated by said complexes;
(d) determining the ratio of signals generated by the 28S rRNA/control probe and 18S rRNA/control probe or the 23S rRNA/control probe and 16S rRNA/control probe or functionally equivalent rRNA/control probe complexes;
(e) assessing the integrity of said sample; and
(f) evaluating microarray analysis results in view of said integrity assessment.

The method of the present invention allows for the assessment of RNA integrity and its relation to microarray analysis performance in an integrated method.

Moreover, the method of the present invention allows the determination of levels of rRNA integrity. One criterion for good quality rRNA in general is that the bands, in case of an agarose gel analysis, not just be present but also be sharply defined. Presumably limited degradation leads to ragged ends as well as complete destruction. Ragged ends are hard to assess quantitatively; they form "shoulders" on the peaks derived from intact rRNAs.

The method according to the present invention allows detection of limited losses of oligo ribonucleotides from the 3' or 5' end of almost intact rRNAs by identification of the position on the immobilized control probes of the rRNA primer. Accordingly, the method according to the present invention provides the assessment of differences in quality between good and perfect total RNA samples with a much higher resolution than provided by the methods as currently known in the art.

DETAILED DESCRIPTION OF THE INVENTION

Before the present method and solutions used in the method are described, it is to be understood that this invention is not limited to particular methods, components, or solutions described, as such methods, components, and solutions may, of course, vary.

In the present specification and the appended claims, the singular forms "a", "an", and "the" include plural references unless the context clearly dictates otherwise.

It should also be understood that the terminology used herein is not intended to be limiting, since the scope of the present invention will be limited only by the appended claims.

Accordingly, definitions should not be understood to limit the scope of the invention. Rather, they should be used to interpret the language of the description and, where appropriate, the language of the claims. These terms may also be understood more fully in the context of the description of the invention. If a term is included in the description or the claims that is not further defined within the present description, or that cannot be interpreted based on its context, then it should be construed to have the same meaning as it is understood by those skilled in the art.

The subject invention lies in the field of nucleic acids and is directed in particular to methods for determining whether a specific nucleic acid sequence is present in a sample. It is important to be able to determine whether the sequence to be detected was in fact absent in the original sample or has been degraded during the method steps the sample has been subjected to, thereby leading to a false negative result. As any person skilled in the art will acknowledge, RNA is extremely sensitive to degradation. In particular in clinical diagnoses on the nucleic acid level a quality control of the nucleic acid that is extracted from such a sample is an important issue.

The present invention relates in particular to a method for integrated nucleic acid integrity assessment and analysis comprising employing a combined array of nucleic acid molecules immobilized on a solid support whereby said array of nucleic acid molecules comprises a combination of oligo's complementary to a RNA derived from 16S or 18S or a functionally equivalent rRNA and oligo's complementary to a RNA derived from 23S or 28S rRNA or a functionally equivalent rRNA as well as detector oligo's complementary to mRNA.

It is current practice in gene expression studies to measure mRNA expression profiles. Cells regulate the expression of their genes in response to changes in their environment. Specific patterns of gene expression, as measured by levels of mRNA production, can provide significant insights into normal tissue development, biological responses, and disease pathogenesis. Gene expression profiling plays a role in streamlining several critical steps in modern pharmaceutical development, new target gene identification, lead drug identification and optimisation, drug toxicity profiling, and monitoring clinical trials.

With state-of-the-art DNA array (DNA chip) technology, scientists are able to immobilize from thousands to tens of thousands of genes onto to a very small surface area. When hybridised with samples of interest, scientists are able to detect and measure expression levels of these thousands of genes with high resolution.

Genes which code for protein are transcribed into mRNA's in the cell nucleus. The mRNA's in turn are translated into proteins by ribosomes in the cytoplasm. The transcription level of a gene is taken to be the amount of its corresponding mRNA present in the cell. In comparative hybridisation experiments for example the amounts of many different mRNA's in at least two cell populations are compared.

Typically in microarray analysis methods, rRNA levels are not measured because rRNAs are not polyadenylated, and so are not converted into cDNA by reverse transcriptase from an oligo dT primer (which also adds e.g. a T7 promoter). Therefore the rRNAs are not amplified or labelled (e.g. by fluorophore) in conventional RNA amplification methods such as described by Van Gelder et al. In U.S. Pat. No. 5,545,522; herewith incorporated by reference.

Typically the first step in making aRNA is to extend an oligo dT primer annealed to the 3' polyA tract of mRNAs to make the first strand cDNA. Most array amplifications use total RNA wherein the rRNA is still present.

In the methods according to the present invention, besides the oligo-dt primer that specifically hybridises to the mRNA the reverse transcriptase reaction is seeded with at least two additional primers that specifically hybridise to the 18S or 16S rRNAs or a functionally equivalent rRNA and to 23S or 28S rRNAs or a functionally equivalent rRNA.

A sample as used in the present invention may be biological material or any material comprising biological material from which ribonucleic acids or total RNA may be prepared and analysed for the qualitative and quantitative presence of particular nucleic acid sequences.

Total RNA may be isolated from virtually any sample. However, usually, the sample is a biological or a biochemical sample. The term "biological sample," as used herein, refers to a sample obtained from an organism or from components (e.g., cells) of an organism. The sample may be of any biological tissue or fluid. Frequently the sample will be a "clinical sample" which is a sample derived from a patient including humans and animals. Such samples include, but are not limited to, bone marrow, cerebrospinal fluid, blood, blood fractions such as serum including foetal serum (e.g., SFC) and plasma, blood cells (e.g., white cells), tissue or fine needle biopsy samples, urine, peritoneal fluid, and pleural fluid, or cells therefrom. Biological samples may also include plant samples and microbial samples including sections of tissues or cells. Methods for the isolation of total RNA from a variety of eukaryotic samples including samples of human, animal, plant and yeast origin are well known in the art.

Accordingly, in one embodiment of the present invention, a method is provided, wherein the sample is a total ribonucleic acid sample.

Accurate gene expression analysis requires the analysis of specific cell types without interference from surrounding cells. Starting with these pure cell populations often means working with small samples. Special technologies are needed to overcome the challenges of handling these precious samples. The combination RNA amplification, and microarray analysis reveals differential gene expression between cell types. Various total RNA amplification methods allowing molecular analysis on RNA samples that are too small for microarray analysis such as microscopic samples are well known in the art.

Accordingly, in one embodiment of the present invention, a method is provided wherein analyte ribonucleic acids are amplified ribonucleic acids.

As mentioned above, the RNA that is used in typical pre-reverse transcription reaction is total RNA, 80% of which is ribosomal RNA. The mRNA component of total cellular RNA can vary from 2% to 5% depending on the tissue, the remainder of the RNA consisting of tRNA or small nuclear RNAs.

Isolation of intact RNA is essential for many techniques used in gene expression analysis such as microarray analysis. RNA of extremely high integrity is required and therefore RNA integrity assessment is an essential part of gene expression analysis. The present invention thereto provides a method for integrated nucleic acid integrity assessment and analysis comprising employing a combined array of nucleic acid molecules immobilized on a solid support whereby said array of nucleic acid molecules comprises a combination of complementary control oligo's to on the one hand the amplified RNA derived from 18S or 16S rRNA or a functionally equivalent rRNA and on the other hand complementary control oligo's from 23S or 28S rRNA or a functionally equivalent rRNA as well as detector oligo's complementary to mRNA.

Accordingly, in one embodiment of the present invention, a method is provided wherein amplified ribonucleic acids are comprised of amplified ribosomal and messenger ribonucleic acids.

In a further embodiment of the present invention, a method is provided wherein amplified ribosomal ribonucleic acids are comprised of amplified 28S and 18S or 23S and 16S or functionally equivalent ribonucleic acids.

It will be appreciated that the amplified analyte ribonucleic acids used in the methods of the present invention may be labelled in order to allow detection of analyte ribonucleic acid/probe complexes on the microarray.

Accordingly, in one embodiment of the present invention, methods are provided wherein amplified analyte ribonucleic acids are labelled.

The term label as used in the present specification refers to a molecule propagating a signal to aid in detection and quantification. Said signal may be detected either visually (e.g., because it has a coloured product, or emits fluorescence) or by use of a detector that detects properties of the reporter molecule (e.g., radioactivity, magnetic field, etc.). In the present specification, labels allow for the detection of the identification and quantification of analyte sequences within a sample. Detectable labels suitable for use in the present invention include but are not limited to any composition detectable by spectroscopic, photochemical, biochemical, immunochemical, electrical, optical or chemical means.

Accordingly, virtually any label that produces a detectable, quantifiable signal and that is capable of being attached to a nucleotide and/or incorporated into the generated amplicon or RNA copy, can be used in conjunction with the methods of the invention. Suitable labels include, by way of example and not limitation, radioisotopes, fluorophores, chromophores, chemiluminescent moieties, chemical labelling such as ULS labelling (Universal Linkage system; Kreatech) and ASAP (Accurate, Sensitive and Precise; Perkin Elmer), etc. Suitable labels may induce a colour reaction and/or may be capable of bio-, chemi- or photoluminescence.

Useful labels in the present invention include for instance biotin for staining with labelled streptavidin conjugate, digoxigenin, anti-digoxigenin, luciferase, P-galactosidase, antigens, enzymes and enzyme conjugates, (e.g. horseradish peroxidase, alkaline phosphatase and others commonly used in e.g. ELISA).

Additional useful labels include isotopic labels including radiolabels (e.g. $^{3}H$, $^{125}I$, $^{35}S$, $^{14}C$, $^{33}P$ or $^{32}P$), calorimetric labels such as colloidal gold (e.g. gold particles in the 40 nm to 80 nm diameter size range scatter green light with high efficiency), sugars, and lectins may also be useful. Patents teaching the use of such labels include U.S. Pat. Nos. 3,817,837; 3,850,752; 3,939,350; 3,996,345; 4,277,437; 4,275,149; and 4,366,241. Molecules that change their fluorescence or activity upon a change in binding may also be useful.

Fluorescent labels are particularly suitable because they provide very strong signals with low background. Fluorescent labels are also optically detectable at high resolution and quick scanning procedure. Fluorescent labels offer the additional advantage that irradiation of a fluorescent label with light can produce a plurality of emissions. Thus, a single label can provide for a plurality of measurable events.

Fluorescent labels are easily added during an in vitro transcription reaction. Thus, for example, fluorescein labelled UTP and CTP may be incorporated into the RNA produced in an in vitro transcription.

Accordingly, in one embodiment of the present invention, methods are provided wherein amplified analyte ribonucleic acids are fluorescently labelled.

Desirably, fluorescent labels should absorb light above about 300 nm, usually above about 350 nm, and more usually above about 400 nm, usually emitting at wavelengths greater than about 10 nm higher than the wavelength of the light absorbed.

Particular useful fluorescent labels include, by way of example and not limitation, fluorescein isothiocyanate (FITC), rhodamine, malachite green, Oregon green, Texas Red, Congo red, SybrGreen, phycoerythrin, allophycocyanin, 6-carboxyfluorescein (6-FAM), 2',7'-dimethoxy-4',5'-dichloro-6-carboxyfluorescein (JOE), 6-carboxy X-rhodamine (ROX), 6-carboxy-2',4',7',4,7-hexachlorofluorescein (HEX), 5-carboxyfluorescein (5-FAM), N,N,N',N'-tetramethyl-6-carboxyrhodamine (TAMRA), cyanine dyes (e.g. Cy5 and Cy3, including e.g. Oyster® dyes by Flownamics®, Madison), BODIPY dyes (e.g. BODIPY 630/650, Alexa542, etc.), green fluorescent protein (GFP), blue fluorescent protein (BFP), yellow fluorescent protein (YFP), red fluorescent protein (RFP), and the like, (see, e.g. Alexa dyes by Molecular Probes, Eugene, Ore., USA; Dyomics, Germany).

In a further embodiment, methods according to the present invention are provided wherein amplified analyte ribonucleic acids are labelled with a fluorescent label chosen from the group including fluorescein, Cy5 and Cy3.

Preferably, the position of the label will not interfere with generation, hybridisation, detection or other post-hybridisation modification of the labelled polynucleotide. A variety of different protocols may be used to generate the labelled nucleic acids, as is known in the art, where such methods typically rely on the labelled primers, or enzymatic generation of labelled nucleic acid using a labelled nucleotide. For instance, label may be incorporated into a nucleic acid during transcription/amplification steps in order to produce labelled amplicons. Therefore, it will be appreciated that the nucleotides used in the methods of the present invention may be labelled.

Accordingly in one embodiment of the present invention, methods are provided wherein analyte ribonucleic acids are labelled by means of labelling-by-synthesis.

Non-limiting examples of labelling-by-synthesis methods are e.g. the methods as disclosed by Van Gelder et al. In U.S. Pat. No. 5,545,522 and e.g. the "Tyras" method as disclosed by Van Gemen in European Patent No. 1 056 884; hereby incorporated by reference.

In the methods according to the present invention, the RNA amplification or reverse transcriptase reaction mixture comprises besides an oligo dT primer two additional primers, having a sequence specific to 18S or 16S rRNA or a functionally equivalent rRNA on the one hand and to 28S or 23S rRNA or a functionally equivalent rRNA on the other hand. Particular suitable rRNA specific primers are designed against non-polymorphic regions of rRNAs; e.g. human rRNAs so the methods according to the present invention are universal for all human total RNA samples or total RNA samples from other organisms. Extension of the primers by an RNA polymerase promoter sequence allows labelling during synthesis of multiple RNA copies complementary to the template rRNAs present in the reaction mixture. A "template" is a nucleic acid molecule that is being copied by a nucleic acid polymerase. A template may be either single-stranded, double-stranded or partially double-stranded, depending on the polymerase. The synthesized copy is complementary to the template or to at least one strand of a double-stranded or partially double-stranded template. Both RNA and DNA are always synthesized in the 5' to 3' direction and the two strands of a nucleic acid duplex always are aligned so that the 5' ends of the two strands are at opposite ends of the duplex (and, by necessity, so then are the 3' ends).

A "promoter sequence" is a specific nucleic acid sequence that is recognized by a DNA-dependent RNA polymerase ("transcriptase" or "RNA polymerase") as a signal to bind to the nucleic acid and to begin the transcription of RNA in the 5'→3' direction at a position just downstream of the promoter. For binding, such transcriptases generally require DNA which is double-stranded in the portion comprising the promoter sequence and its complement; the template portion (sequence to be transcribed) need not be double-stranded. Individual DNA-dependent RNA polymerases recognize a variety of different promoter sequences which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence. The promoter may be the promoter for any suitable RNA polymerase. The present invention intends to use an "enzyme having RNA polymerase activity", such as for instance, the RNA polymerases from *E. coli* and bacteriophages T7, T3 and SP6. Accordingly, the promoter sequences that are recognised by the RNA polymerases from *E. coli* and bacteriophages T7, T3 and SP6 are contemplated in the oligonucleotides of the invention. The processivity of, for example, the T7 RNA polymerase is very high, usually more than 250 nucleotides per second on a DNA template. This means that the amplification rate is determined by the number of initiation events per promoter, per time unit. Since the promoter is identical for each target RNA there is no selectivity in the amplification. By application of the RNA polymerase, new RNA copies of the original target RNA are made. During the transcription step, typically 10-1000 copies of each RNA are being made.

As disclosed by Van Gelder et al. in U.S. Pat. No. 5,545,522 cDNA strands may be synthesized from a collection of RNA molecules using a primer linked to a promoter region. This promoter region is located upstream of the primer at its 5' terminus in an orientation permitting transcription with respect to the RNA population utilized. When the second cDNA strand is synthesized, the promoter sequence will be in correct orientation in that strand to initiate RNA synthesis using that second cDNA strand as template.

Alternatively, particular suitable methods for the amplification of RNA do not need the production of cDNA intermediates as basis for the amplification as is described by Van Gemen in EP 1 056 884 B1. In this so-called "Tyras" method the RNA is synthesized by an RNA polymerase, directly from the target RNA template present in the material under investigation. The activity of the RNA polymerase is independent from any secondary structures present in the target RNA and thus there are no differences in the way the different target RNAs are amplified depending on structures in the target RNAs. In this method, in order to prevent any extension along the RNA template, the oligonucleotide may be blocked at its 3' end. As such, reverse transcriptase will not be able to start extension of the blocked 3' end of the oligonucleotide and no cDNA is synthesized at this side.

The 3' terminus of the oligonucleotide can be blocked in a variety of ways, including by a modification at its 3' terminal end. The modification at the 3' terminal end of the oligonucleotide can be accomplished by, for instance, having a 3'-terminal sequence non-complementary to the target RNA, or by having a biotin-group, or by having a modified nucleotide, such as a 3'-terminal dideoxynucleotide, Rp-NTP-α-S phosphorothioate nucleotide isomer and nucleotides comprising alkane-diol residues, cordycepins or amino-alkyls, or in other ways well known to those skilled in the art.

Accordingly, in one embodiment of the present invention, methods are provided wherein labelling-by-synthesis comprises the steps of (a) providing total ribonucleic acid sample and contacting said sample with:
   (i) a set of ribonucleic acid-specific primers comprising a promoter sequence recognized by an RNA polymerase;
   (ii) an enzyme having RNA polymerase activity;
   (iii) sufficient amounts of rNTPs;
   wherein either said primers of (i) or said NTPs of (ii) are labelled; and
(b) maintaining the resulting reaction mixture under the appropriate conditions for a sufficient amount of time for the enzymatic processes to take place.

Unlike the oligo dT primers, the rRNA primers may be end-labelled wherein a label is attached to either 3' or 5' end of the oligonucleotide; e.g. T4 polynucleotide kinase may be used to catalyze the transfer of labelled phosphate from a nucleoside donor to the 5'-hydroxyl group of a polynucleotide, oligonucleotide or nucleoside. Alternatively, the rRNA primers may be equally end-labelled with a photostable fluorescent dye. These primers will allow synthesis of a single stranded cDNA proportionate to the concentration of the rRNA. These primers are usually blocked to make the cDNA resistant to degradation by Dnase1.

Accordingly in a further embodiment of the present invention, methods are provided wherein amplified analyte ribonucleic acids are end-labelled.

An alternative to co-amplification of rRNA with mRNA is provided by so-called stacking whereby unamplified rRNA present in the sample after mRNA amplification is directly captured and then detected by one or more fluorescent oligonucleotides in solution binding to the captured rRNA in a spot.

Means for detecting attached and/or incorporated labels are well known to those of skill in the art. Thus, for example, radiolabels may be detected using photographic film or scintillation counters; fluorescent markers may be detected using a photodetector to detect emitted illumination. Enzymatic labels are typically detected by providing the enzyme with an enzyme substrate and detecting the reaction product produced by the action of the enzyme on the substrate; colorimetric labels are detected by simply visualizing the coloured label, and chemical labels by for example a platinum group forming coordinative bonds with the labelling target, firmly coupling the label to the target.

In the methods according to the present invention, primer sequences are predetermined to specifically hybridise to on the one hand 18S or 16S rRNA or a functionally equivalent rRNA and on the other hand 28S or 23S rRNA or a functionally equivalent rRNA and primer sequences predetermined to specifically hybridize to mRNA.

Accordingly, in one embodiment of the present invention, methods are provided wherein the set of ribonucleic acid-specific primers comprises ribosomal and messenger ribonucleic acid-specific primers.

rRNA levels can be measured on an array upon amplification by reverse transcriptase whereby rRNA specific primers are being used. The copies made represent the original target RNA population as present in the starting material. A disadvantage is that often in amplification reactions of total RNA, the rRNA abundance causes a loss of exponential amplification for the mRNA template of much lower abundance resulting in the loss of quantitative information; i.e. resources such as NTPs and RNA polymerase would be diverted from mRNA amplification.

Reducing the signal of the rRNA (or cDNA derived therefrom) preferably therefore is performed at the level of transcription. In the present invention, rRNA primers have an RNA polymerase promoter extension. However, it is not a wild-type promoter; initiation at such a promoter would lead to an overwhelming strong signal and would divert resources (NTPs, RNA polymerase) from mRNA amplification. Therefore the promoters used on the rRNA primers are mutated which initiates the RNA polymerase less efficiently.

Accordingly, in one embodiment of the present invention, methods are provided wherein ribosomal ribonucleic acid-specific primers comprise a mutated promoter sequence; said mutated promoter sequence causing the RNA polymerase to initiate the polymerization reaction less efficiently. Initiation here is used to include binding of the promoter by the RNA polymerase and also the early steps of promoter clearance when a short transcript (<20 nucleotides) is synthesised but the full promoter clearance into a fully productive elongation complex has not yet been achieved.

The use of mutated promoters causes the RNA polymerase to initiate less efficiently. As such, in vitro transcription of the rRNA species is inefficient compared to the more efficient wild-type promoter amplifying the mRNAs. Basically, for use in the methods of the present invention, the promoter driving the amplification of mRNA is more efficient than the one driving the amplification of the rRNA. Promoters with decreased efficiency include for example point-mutated promoters and promoters with nucleotide additions or deletions. These mutations may be in regions that bind the RNA polymerase directly or in the region where transcription is initiated. Mutated promoters that negatively affect/down-regulate promoter efficiency are well known in the art.

Certain promoter mutations as shown in Table 1 are known to reduce transcription either by reducing binding of the T7 RNA polymerase or in clearing the promoter region and forming a productive elongation complex (Milligan J F, Goebe J R, Witherell G W and Uhlenbeck O C, 1987, "Oligoribonucleotide synthesis using T7 RNA polymerase and synthetic DNA template", Nucl. Acids Res. 15: 8783-8798; McGinness K E, Joyce G F, 2002, "Substitution of ribonucleotides in the T7 RNA polymerase promoter element", J. Biol. Chem 277: 2987-2991.). The sequence as shown by SEQ ID NO.1 (Table 1) is the minimal DNA sequence of a wild-type T7 promoter, as is typically used in the Van Gelder/Eberwine amplification as disclosed in U.S. Pat. No. 5,545, 522. The G residue underlined is the +1 nucleotide, the point at which where transcription initiates. The A residue to the left is the −1 residue, the T to the left of that is the −2 position and so on, counting backwards from the initiation point. If the initiation region is deleted or mutated (SEQ ID NO. 2 in Table 1, critical residues that can be changed are underlined) then this can often reduce the initiation of transcription to differing extents depending on the precise mutation. Alternatively, mutations (e.g. single changes at critical residues) within the upstream initiation region (underlined in SEQ ID NO. 3, Table 1) can also down-regulate transcription. Further, mutations which change T or A residues to G or C residues within the TA rich region tend to down-regulate transcription (underlined in SEQ ID NO. 4, Table 1). Other positions are relatively tolerant of mutation (e.g. underlined in SEQ ID NO. 5, Table 1, such as the −10 and −11 GA residues). SEQ ID NO. 6 (Table 1) shows the −7 to −9 residues underlined; mutations in this region often strongly down-regulate transcription. As will be well appreciated in the art, similar mutation strategies can be applied with other promoters (e.g. T3 or SP6) though the exact mutations required accomplishing this task may differ individually.

Alternatively, primers that anneal poorly (but very specifically) may be used in order to compensate for any competition for the reverse transcriptase. Examples of suitable primers may contain a degree of secondary structure (e.g. containing moderately stable stem loops) or may hybridise to a region in the rRNA which have secondary structure.

As will be appreciated by skilled persons, suitable RNA polymerases used in the present invention are well known in the art and include by way of example and not limitation bacteriophage and bacterial T7, T3 SP6 RNA polymerase, and multi subunit polymerases from bacteria or from eukaryotes. Suitable polymerases include bacterially derived DNA-dependent RNA polymerases. Also thermostable RNA polymerases either from naturally occurring organisms (e.g. thermophilic bacteria such as Thermus RNA polymerase from Epicentre) or selected mutated from less thermostable polymerases (e.g. thermostable mutants to T7 RNA polymerase) are suitable. Similarly, other RNA polymerases able to perform amplification reactions under extreme conditions as well as appropriate RNA polymerises from eukaryotes or eukaryotic viruses are suitable for use in the methods according to the present invention.

Accordingly, in one embodiment of the present invention, methods are provided wherein RNA polymerase is chosen from the group including single-subunit phage RNA polymerases, DNA-dependent bacterial RNA polymerases, thermostable RNA polymerases, eukaryotic RNA polymerases and viral RNA polymerases.

In a further embodiment of the present invention, methods are provided wherein RNA polymerase is chosen from the group including T7, SP6 and T3 RNA polymerases.

For improved reproducibility and accuracy of procedures, an automated system for determining gene expression profiles is contemplated. In particular, the present invention connotes the use of a probe array which is interrogated with the multiple RNA copies provided by the methods of the invention. The term "probe array" relates to a support having a matrix pattern of positionally defined specific recognition reagents.

In an array format a large number of different hybridisation reactions can be run essentially "in parallel." This provides rapid, essentially simultaneous, evaluation of a number of hybridisations in a single "experiment". Methods of performing hybridisation reactions in array-based formats are well known to those skilled in the art.

The multiple RNA copies provided by the method of the invention are capable of interacting, e.g. hybridising, with their specific counterparts, i.e. the specific recognition reagents, on the array. Because the specific recognition reagents are positionally defined, the sites of interaction will define the specificity of each interaction. The specific recognition reagents will typically be oligonucleotide probes, in which case said probe array is known as an oligonucleotide array.

The term "nucleic acid" as used herein means a polymer composed of nucleotides, e.g. deoxyribonucleotides or ribonucleotides. The terms "ribonucleic acid" and "RNA" as used herein means a polymer composed of ribonucleotides. The terms "deoxyribonucleic acid" and "DNA" as used herein means a polymer composed of deoxyribonucleotides. The term "oligonucleotide" as used herein denotes single stranded nucleotide multimers of from about 10 to about 100 nucleotides in length. The term "polynucleotide" as used herein refers to single or double stranded polymer composed of nucleotide monomers of from about 10 to about 100 nucleotides in length, usually of greater than about 100 nucleotides in length up to about 1000 nucleotides in length.

The arrays of the present invention may be of any desired size, from two spots to $10^6$ spots or even more. The upper and lower limits on the size of the support are determined solely by the practical considerations of working with extremely small or large supports.

For a given support size, the upper limit is determined only by the ability to create and detect the spots in the array. The preferred number of spots on an array generally depends on the particular use to which the array is to be put. For example, mutation detection may require only a small array. In general, arrays contain from 2 to about $10^6$ spots, or from about 4 to about $10^5$ spots, or from about 8 to about $10^4$ spots, or between about 10 and about 2000 spots, or from about 20 to about 200 spots.

The immobilized polynucleotides may be as few as four, or as many as hundreds, or even more, nucleotides in length. Contemplated as polynucleotides according to the invention are nucleic acids that are typically referred to in the art as oligonucleotides and also those referred to as nucleic acids. Thus, the arrays of the present invention are useful in applications where the generated RNA copies acids are hybridised to immobilized arrays of relatively short probes (such as, for example, having a length of approximately 6, 8, 10, 20, 40, 60, 80, or 100 nucleotides).

The oligonucleotides used on the microarrays are typically prepared using previously genetically or physically mapped sequences. For example, sequence tagged sites (STS) which are used to "tag," or identify particular DNA segments in the genome can be used. To assign an STS designation, each cloned DNA segment is sequenced over an approximately 200 to 500 base pair region. With this sequence data, PCR primers are designed and tested to ensure they can be used to identify, "tag", or synthesize that particular sequence by PCR amplification. Submission of segment and primer sequences, and PCR assay conditions to public databases allows anyone to rapidly and conveniently identify virtually any genomic clone or fragment. See, for example, Olson, Science 245: 1434-1435 (1989). Alternatively, expressed sequence tags (EST) can be used to prepare the arrays of the invention.

The present invention connotes the use of a combined probe or oligonucleotide array. In particular, the set of immobilized polynucleotides on the arrays used in the methods according to the present invention are comprised of detector probes and control probes for hybridisation of amplified RNA originating from respectively mRNA and rRNA in the sample.

In a particular useful array format, each hybridisation is kept separate; i.e. spots within the array comprise oligonucleotides complementary to either 18S rRNA, 28S rRNA or mRNA and different fluorescent dyes are reserved for samples of different origins (e.g. different tissues) amplified separately and applied to the same array at the same time. Alternatively, under certain circumstances it may be envisaged that spots within the array comprise different oligonucleotide species complementary to amplified rRNA as well as amplified mRNA and different fluorescent dyes are reserved to distinguish 18S rRNA from 28S rRNA from mRNA within a single spot.

Detector probes may correspond to particular mutations that are to be identified in a known sequence. For example, if a particular nucleic acid is known to contain an unidentified mutation at a particular position, then the mutated position can be identified with an array of eight polynucleotides, three corresponding to the three possible substitutions at that position, one corresponding to the deletion of the base at that position, and four corresponding to the insertion of the four possible bases at that position. Alternatively, for a known gene that may contain any of several possible identified mutations, the array may comprise polynucleotides corresponding to the different possible mutations. This is, for instance, useful for genes like oncogenes and tumour suppressors, which frequently have a variety of known mutations in different positions. Using arrays facilitates determining whether or not these genes contain mutations by allowing simultaneous screening with RNA copies of the present invention corresponding to each of these different positions.

Accordingly, an embodiment of the present invention provides methods wherein immobilized detector probes are able to hybridise to amplified messenger ribonucleic acids.

Control probes as used in the present invention are complementary to nucleic acids amplified from sample rRNA. In particular, the present invention connotes the use of control probe sequences which are specific for hybridisation with either 16S or 18S or a functionally equivalent rRNA or with either 23S, 28S or an equivalent RNA.

As such the present invention provides methods wherein the set of at least two control probes comprise at least a first and second control probe. In particular, said first control probe is complementary to amplified 23S or 28S or a functionally equivalent ribonucleic acid and said second control probe is complementary to amplified 16S or 18S or a functionally equivalent ribonucleic acid.

Arrays, particularly nucleic acid arrays can be produced according to a wide variety of methods well known to those of skill in the art. For example "low density" arrays can simply be produced by spotting (e.g. by hand using a pipette) different nucleic acids at different locations on a solid support (e.g. a glass surface, a membrane, etc.). This simple spotting, approach may be automated to produce high density spotted arrays (see, e.g., U.S. Pat. No. 5,807,522). This patent describes the use of an automated system that taps a microcapillary against a surface to deposit a small volume of a biological sample. The process is repeated to generate high density arrays. Microarrays of the invention can also be produced using oligonucleotide synthesis technology according to methods well known to those skilled in the art. For example, Fodor et al. Science 767-773 (1991), U.S. Pat. No. 5,143,854 teach the use of light-directed combinatorial synthesis of high-density oligonucleotide arrays.

The polynucleotides can be immobilized on the support using a wide variety of techniques. For example, the polynucleotides can be adsorbed or otherwise non-covalently associated with the support (for example, immobilization to nylon or nitrocellulose filters using standard techniques); they may be covalently attached to the support; or their association may be mediated by specific binding pairs, such as biotin and streptavidin.

A number of materials suitable for use as supports in the present invention have been described in the art. Particularly suitable materials for use as supports in the present invention include any type of solid supports known in the art. Said solid supports may be porous solid supports known in the art.

The support may be in the form of beads, particles, sheets, films or membranes and may be permeable. For example, the support may consist of bead or particles (such as conventional solid phase synthesis supports), fibres (such as glass wool or other glass or plastic fibres), glass or plastic capillary tubes, or metal oxide membranes. Supports may be planar or have simple or complex shape. In case of porous supports, the surface to which molecules are adhered may be an external surface or an internal surface. Particularly where the surface is porous, the molecule is likely to be attached to an internal surface. Where the solid surface is porous, various pore sizes may be employed depending upon the nature of the system.

A number of materials suitable for use as supports in the present invention have been described in the art. Exemplary suitable materials include, for example, acrylic, styrene-methyl methacrylate copolymers, ethylene/acrylic acid, acrylonitrile-butadienestyrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6-6, nylon 6/9, nylon 6/10, nylon 6/12, nylon 11 and nylon 12), polycarylonitrile (PAN), polyacrylate, polycarbonate, polybutylene terephthalate (PBT), polyethylene terephthalate (PET), polyethylene (including low density, linear low density, high density, cross-linked and ultra-high molecular weight grades), polypropylene homopolymer, polypropylene copolymers, polystyrene (including general purpose and high impact grades), polytetrafluoroethylene (PTFE), fluorinated ethylene-propylene (FEP), ethylene-tetrafluoroethylene (ETFE), perfluoroalkoxyethylene (PFA), polyvinyl fluoride (PVF), polyvinylidene fluoride (PVDF), polychlorotrifluoroethylene (PCTFE), polyethylene-chlorotrifluoro-ethylene (ECTFE), polyvinyl alcohol (PVA), silicon styreneacrylonitrile (SAN), styrene maleic anhydride (SMA), and glass.

Other exemplary suitable materials for use as supports in the arrays of the present invention include metal oxides. Metal oxides provide a support having both a high channel density and a high porosity, allowing high-density arrays comprising different specific recognition reagents per unit of the surface for sample application. In addition, metal oxides are highly transparent for visible light. Metal oxides are relatively cheap supports that do not, require the use of any typical microfabrication technology and, that offers an improved control over the liquid distribution over the surface of the support, such as electrochemically manufactured metal oxide membrane. Metal oxide membranes having through-going, oriented channels can be manufactured through electrochemical etching of a metal sheet. Metal oxides considered are, among others, oxides of tantalum, titanium, and aluminium, as well as alloys of two or more metal oxides and doped metal oxides and alloys containing metal oxides. The metal oxide membranes are transparent, especially if wet, which allows for assays using various optical techniques. Such membranes have oriented through-going channels with well-controlled diameter and useful chemical surface properties. European Patent EP-B1-0 975 427 is exemplary in this respect, and is specifically incorporated in the present invention.

In the methods according to the present invention, the presence of particular nucleic acid sequences in a collection of labelled amplified nucleic acid sequences is determined by hybridising the amplified nucleic acid sequences to an oligonucleotide microarray.

After subtraction of background and appropriate normalisation or other corrections, the signals derived from the ribosomal rRNA-specific probes can be used in calculations that provide indicators as to the quality of the RNA sample. The primary information to be calculated from these data is the comparison between the abundance of the 18S and 28S rRNAs and their functional equivalents, or partially degraded fragments derived from these rRNA. The most convenient expression of such data is as a simple ratio, either in terms of molecules (including but not limited to expressions such as molar, micromolar or nanomolar) or amount (including but not limited to nanograms, micrograms, numbers of nucleotides). Other more advanced analysis techniques such as clustering can also be applied to these data. Within the present invention, it is further understood by the term "ratio" that other numerical methods, for example percentage or fraction, are included. For example, a ratio of 2:1 of 28S to 18S rRNA could also be expressed that the 28S rRNA is said to be 66.7% of the 18S and 28S rRNAs combined. Alternatively, the 18S rRNA could be said to be present at 50% of the amount of the 28S rRNA. As the present invention allows the concentration of different sections of a single rRNA species to be specifically measured other comparisons are possible; these may provide additional information as to RNA quality. For example, the relative abundance of stable and unstable regions (e.g., 5' and 3' end) of an individual rRNA may be measured which is impractical with whole molecule analysis (electrophoresis) based methods. It may of course also be valuable to assay the amount of a specific rRNA and one or more mRNAs.

Within the present invention the hybridisation signal intensity, and the ratio of intensities, produced by the hybridisation events between first control probe/amplified 18S rRNA and second control probe/amplified 28S rRNA is determined. Amplicon ratio analysis for hybridised 28S and 18S amplified rRNA confirms RNA integrity.

Accordingly, an embodiment of the present invention provides methods wherein the ratio of signals which is determined is the ratio of signals generated by the complexes comprising a first control probe to the signals generated by the complexes comprising a second control probe.

Methods according to the present invention allow the analysis of two or more samples onto a single array; each sample being differently labelled. In case of two samples, a first sample may be amplified (mRNA plus rRNA) incorporating one dye and in a completely separate reaction vessel a second sample (again, both mRNA and both rRNAs) may be amplified; this time labelled with a second dye. For example Cy3 and Cy5 are suitable labels though there is no reason to limit this to 2 dyes and 2 samples. After amplification the two samples are mixed and applied to the array, the array is then to be scanned at different wavelengths specific to each dye so the fraction of each sample binding to any given oligonucleotide spot (e.g. a 18S rRNA spot, a mRNA spot or a 28S rRNA spot) can be quantified.

It is another object of the invention to provide for the use of a method according to the present specification and as described herein for microarray analysis of a ribonucleic acid sample.

In a further embodiment, the use of a method according to the present invention and as described herein is provided for simultaneously assessing sample integrity and analysis.

In yet a further embodiment, the use of a method according to the present invention and as described herein is provided for assessing quality of sample ribonucleic acids.

In yet a further embodiment, the use of a method according to the present invention and as described herein is provided for gene expression analysis.

It is another object of the present invention to provide a microarray for analysis of analyte ribonucleic acids derived from a sample comprising a support having immobilized thereon a set of detector probes and a set of at least two control probes, said at least two control probes allowing the assessment of integrity of the sample.

In a embodiment, a microarray is provided as described above wherein said sample is a total ribonucleic acid sample.

In a further embodiment, a microarray is provided as described above wherein said analyte ribonucleic acids are amplified ribonucleic acids.

In yet a further embodiment, a microarray is provided as described above wherein said amplified ribonucleic acids are comprised of amplified ribosomal and messenger ribonucleic acids.

In yet a further embodiment, a microarray is provided as described above wherein said detector probes are complementary to amplified messenger ribonucleic acids.

In yet a further embodiment, a microarray is provided as described above wherein said set of at least two control probes comprise a first control probe and a second control probe.

In yet a further embodiment, a microarray is provided as described above wherein said first control probe is complementary to amplified 23S, 28S or functionally equivalent ribonucleic acids and said second control probe is complementary to amplified 16S, 18S or functionally equivalent ribonucleic acids.

In the analysis of microarray hybridisation results, the absence of rRNA markers obviously would be indicative of degradation but their presence can still occur even though degradation has taken the place of nucleic acid in the sample. Such degradation can however occur to an insufficient degree to ensure that the entire marker rRNA has also been degraded. In case of an agarose gel analysis, limited degradation can lead to ragged ends or presumably other fragments as well as complete destruction. FIG. 1 illustrates different integrity samples: (1) sample A is heavily degraded and on a gel or by Bioanalyzer the 18S rRNA band typically is barely detectable and the 28S rRNA is completely degraded; mRNA is almost completely degraded, usually there is no clearly resolvable band by gel or Bioanalyzer, though there may be truncated fragments of both rRNAs present but these are hard to detect as they are likely to be heterogenous in size; (2) sample B is good but not perfect, both 18S and 28S bands are present but there is limited rRNA degradation and some mRNAs are partially degraded, some of the degraded rRNA is completely lost and some present as fragments; (3) sample C is perfect, the 18S to 28S ratio is ideal (1:2) and there is absolutely no mRNA degradation.

The aspect that degradation can occur to an insufficient degree to ensure that all the marker rRNA has also been degraded is naturally vital in the case of clinical diagnosis as this could lead to a false negative report of the presence of a particular analyte in the sample.

Figure 2:
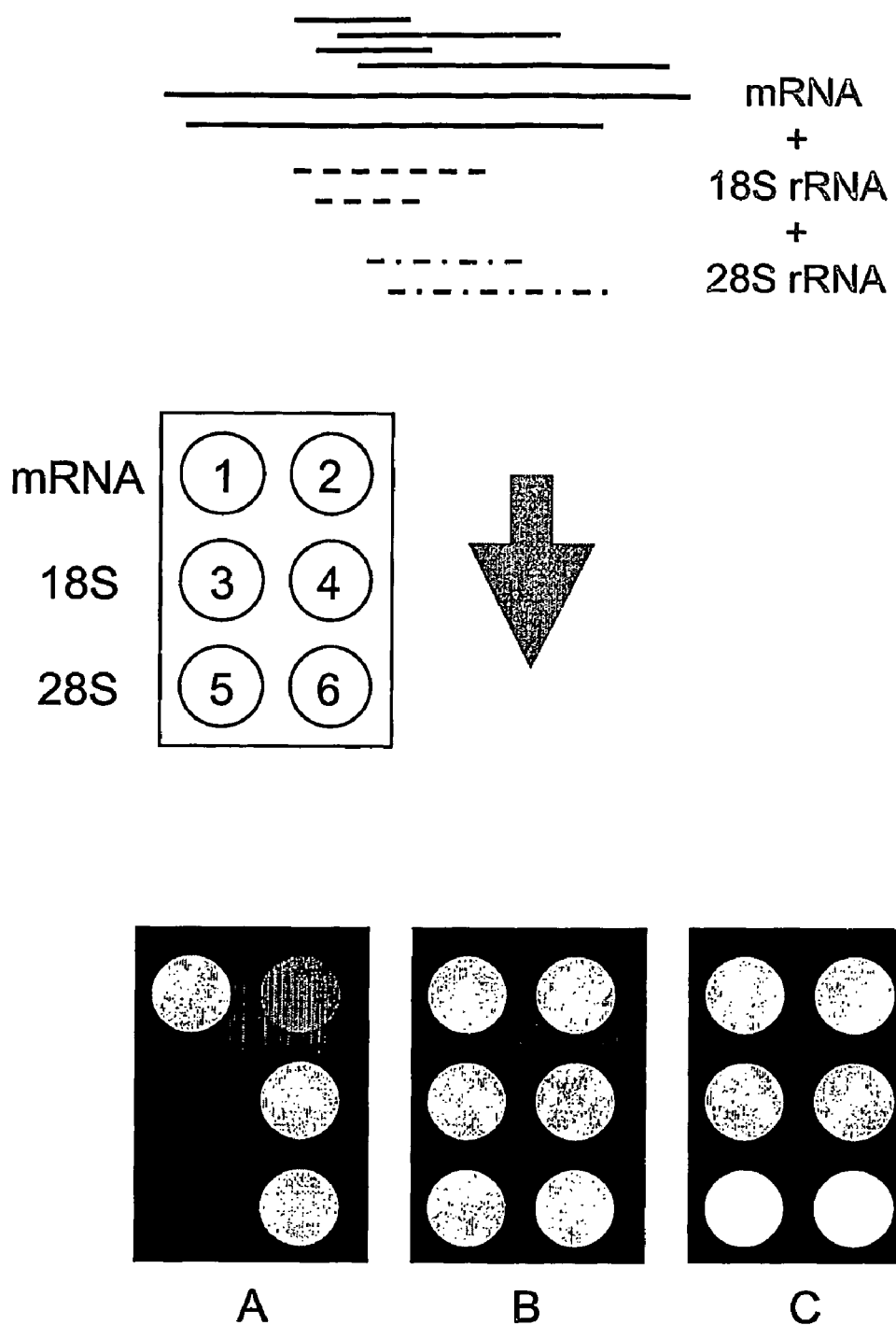

The assessment according to the methods of the present invention of differences in quality between good and perfect total RNA samples is illustrated in FIG. 2. FIG. 2 illustrates a microarray analysis of 3 samples, each sample is amplified separately with rRNA and oligodT (mRNA) primers incorporating a single fluorescent dye and applied to three different but identical arrays. Alternatively, the samples may be labelled with 3 different and distinguishable dyes, mixed and applied to the same array after which the binding at a unique wavelength for each dye is then assessed. In the illustration of FIG. 2, each array has 6 spots printed with oligonucleotides with the following properties: spot 1, a mRNA specific oligonucleotide that hybridises to aRNA from an extremely stable mRNA that survives even poor sample handling; spot 2, mRNA specific oligo that hybridises to aRNA from an extremely unstable mRNA that is very sensitive to degradation in this tissue type; spot 3, oligo that hybridises to amplified 18S rRNA is far more specific for full length 18S rRNA than partially degraded; spot 4, oligonucleotide hybridising to amplified 18S rRNA that binds to full length and also to partially degraded rRNA (i.e. It binds to a relatively stable portion of the rRNA); spot 5, oligonucleotide that binds to amplified 28S rRNA and tends to bind to full length better than to partially degraded rRNA; spot 6, oligonucleotide that binds to amplified 28S rRNA and hybridizes to full length or partially degraded 28S rRNA.

Even if sample A is heavily degraded, the methods according to the present invention allow the detection of the more stable mRNA and degraded rRNAs allowing quantification as to how poor sample A is. For far better samples as samples B and C, methods according to the present invention allow the detection of stable and unstable mRNAs and full length and full length plus degraded rRNAs. Comparison of the ratio of signals from 28S and 18S-specific oligonucleotides, it is clear that C is a more intact sample than B. Thus comparison of signal strength of hybridisation to oligonucleotides 3 and 4 (for 18S rRNA) and 5 and 6 (for 28S rRNA) allows quantification of partially degraded rRNA.

Methods according to the present invention provide for a further fine-tuning with respect to the original sample quality.

In general, it is difficult to resolve and quantify partially degraded rRNA by Bioanalyzer or by gel. Limited degradation leads to a smearing or shoulder as a small number of nucleotides are removed from one or both ends; but even from undegraded rRNA this is difficult to resolve. More extreme degradation leads to (often heterogenous) fragments that blend with the mRNA which are also a wide variety of lengths and tend to form a smear.

The methods of the present invention, however allow, by appropriate oligonucleotides probe design (e.g. oligonucleotides on the microarray against the extreme 5' and 3' of each rRNA and oligonucleotides hybridising to stable and unstable internal regions), to perform an array based QC method which is far more sensitive to subtleties in rRNA degradation compared to known methods in the art.

Furthermore, methods according to the present invention anticipate different types of sample mishandling to be diagnosed; for example, methods according to the present invention are sensitive to the removal of e.g. 30 nucleotides from one end of a rRNA. This allows distinguishing good from perfect samples where a small number of nucleotides have been removed by limited RNAse activity. Further, different sample handling problems such as e.g. Improper sample storage, delay before storage or poor RNA extraction procedures may lead to different types of rRNA degradation fingerprints. As such, "fingerprint" QC may be developed that helps reports on the reasons a sample may be degraded.

Depending on the position of the immobilized control probe and the primer comprising rRNA specific and RNA polymerase promoter sequences, the methods according to the present invention allow for the identification/determination of oligoribonucleotide losses from the 3' and/or 5' end of the almost intact rRNAs.

Accordingly, a microarray is provided according to the present invention and as described herein wherein said control probes are complementary to rRNA regions chosen from the group including the extreme 5' and 3' regions of each rRNA and stable and unstable internal regions.

Accordingly, a method according to the present invention is provided wherein control probes are complementary to rRNA regions chosen from the group including the extreme 5' and 3' regions of each rRNA and stable and unstable internal regions.

It will be well appreciated that microarrays used in the methods of the present invention may be integrated microarrays and part of devices for the analysis of sample nucleic acids.

Handling microarrays is greatly improved by means of a device for holding microarrays such as described for example in WO 02/072268 which is herewith incorporated by reference.

High-throughput analysis of numerous samples simultaneously may be accommodated by a system such as described for example in international Application No. PCT/EP03/ 50114, herewith Incorporated by reference, which discloses a system for conducting bioassays, comprising a support plate with a number of wells, and an incubation device for holding the plate. This known analytical test device is composed of a plastic support wherein openings in the plastic support define wells with a certain diameter, said wells being open at the top for sample or probe application and having a support defining the bottom of each well. Said support may be a microarray as described in the present specification.

A system as described above allows for parallel processing of a large number of genomic nucleic acid samples and may be applied in automated robotic platforms. Such system usually comprises a microplate with an array of wells arranged in rows and columns, wherein the bottom of each well is a matrix having a flow-through fibre network. Using for example a microplate with an array of ninety-six wells allows a parallel processing of a large number of hybridisations resulting in a very efficient high-throughput analysis Accordingly, it is another object of the present invention to provide for devices for analysis of analyte ribonucleic acids derived from a sample comprising a microarray as disclosed and described within the present specification.

Moreover, the present invention relates to kits for microarray analysis of analyte ribonucleic acids derived from a sample comprising a device as disclosed within the present specification and instructions to carry out the methods as disclosed within the present specification.

In addition, the present invention relates to kits as described above, which further comprise a set of ribonucleic acid-specific primers, each ribonucleic acid-specific primer comprising a promoter sequence recognized by an RNA polymerase; optionally, an enzyme having RNA polymerase activity; and optionally, an amount of rNTPs.

Further in addition, the present invention relates to kits as described above, wherein said set of ribonucleic acid-specific primers comprise ribosomal and messenger ribonucleic acid-specific primers.

Further in addition, the present invention relates to kits as described above, wherein said ribosomal ribonucleic acid-specific primers comprise a mutated promoter sequence: said mutated promoter sequence causing the RNA polymerase to initiate the polymerization reaction less efficiently.

It will be well appreciated that data generated by methods according to the present invention may be further processed in automated or integrated software packages that (automatically) interpret the rRNA data for further use in the interpretation of mRNA expression patterns.

Analysis of microarrays as used in the methods and systems according to the present invention may be performed by a scanning system which may operate under the direction of an appropriately programmed digital computer, which may or may not be the same computer as the computer used in the analysis. The scanner typically includes a detection device such as a confocal microscope or CCD (charge-coupled device) that is used to detect the locations on the array where labelled analyte nucleic acids have bound to the support. The output of the scanner is an image file(s) indicating, in the case of fluorescein labelling, the fluorescence intensity as a function of position on the support.

The image file(s) is provided as input to an analysis system that incorporates the visualisation and analysis methods of the present invention. The analysis system may be any of a wide variety of computer systems.

Accordingly, it is a further object of the present invention to provide a computer program product that identifies expression level of a sample nucleic acid comprising:

(a) computer code that receives a plurality of signals corresponding to analyte ribonucleic acid intensities for a plurality of analyte ribonucleic acids, each analyte ribonucleic acid intensity indicating an extend of hybridisation of an analyte ribonucleic acid with an immobilized detector probe;
(b) computer code that receives at least two signals corresponding to analyte ribonucleic acid intensities for 16S, 18S or a functionally equivalent and 23S, 28S or a functionally equivalent analyte ribonucleic acids, each analyte ribonucleic acid intensity indicating an extent of hybridisation of a 16S, 18S or functionally equivalent ribonucleic acid or and extent or hybridisation of a 23S, 28S or a functionally equivalent analyte ribonucleic acid with a complementary immobilized control probe;
(c) computer code that performs a comparison and calculates the ratio of said at least two signals of step (b);
(d) computer code that performs a correction of said plurality of analyte ribonucleic acid intensities of step (a) according to said ratio as determined in step (c); and
(e) a computer readable medium that stores said computer codes.

Typically, as well known in the art, the ratio of intensities of signals coming from hybridisations between rRNA and corresponding immobilized control probes is calculated as the intensity of hybridisation of 28S RNA to its corresponding control probe to the intensity of hybridisation of 18S RNA to its corresponding control probe; i.e. 28S:18S intensity ratio.

Immobilized detector and control probes as mentioned in the above computer program are usually arranged in an array format with detector and control probes immobilized at spatially distinguishable addresses within the array. Usually, each spatially distinguishable address or spot within an array is comprised of one oligonucleotide species which is complementary to either analyte mRNA, 18Sr RNA or 28S rRNA.

Intensities received by computer codes within computer program products according to the present invention are usually fluorescent intensities.

Suitable computers may be appropriately programmed Sun Workstation or personal computer or workstation, such as IBM PC equivalent, including appropriate memory and a CPU. The computer system may obtain inputs regarding characteristics of genes of interest, and other inputs regarding the desired features of the array. Optionally, the computer system may obtain information regarding a specific genetic sequence of interest from an external or internal database such as GenBank. The output of the computer system is a set of chip design computer files in the form of, for example, a switch matrix.

It is a further object of the present invention to provide for a system that identifies expression level of a sample nucleic acid comprising:

(a) a microarray according to the present invention and as described herein;
(b) a processor;
(c) a computer readable medium coupled to said processor for storing a computer program comprising
  i. computer code that receives a plurality of signals corresponding to analyte ribonucleic acid intensities for a plurality of analyte ribonucleic acids, each analyte ribonucleic acid intensity indicating an extend of hybridisation of an analyte ribonucleic acid with an immobilized detector probe;
  ii. computer code that receives at least two signals corresponding to analyte ribonucleic acid intensities for 18S and 28S analyte ribonucleic acids, each analyte ribonucleic acid intensity indicating an extent of hybridisation of a 18S or 28S analyte ribonucleic acid with a complementary immobilized control probe;

iii. computer code that performs a comparison and calculates the ratio of said at least two signals of step (b);

iv. computer code that performs a correction of said plurality of analyte ribonucleic acid intensities of step (a) according to said ratio as determined in step (c);

The above is provided to illustrate the invention but not to limit its scope. Other variants of the invention will be readily apparent to one of ordinary skill in the art and are encompassed by the appended claims. The content of all documents cited above is hereby incorporated by reference.

SHORT DESCRIPTION OF THE FIGURES

FIG. 1 is a schematic representation of an agarose gel analysis of samples A to C having different integrity ranging from highly degraded (sample A) to perfectly intact (sample C). For the sake of clarity, the mRNA smear is shown as similar in each sample; in reality it would be of smaller average length in the more degraded samples. The arrow indicates sample quality.

FIG. 2 is a schematic representation of a microarray analysis showing the outcome of hybridised amplified RNA (both mRNA and rRNA) from samples A to C. Sample A is badly degraded; sample B is of good integrity and sample C is of perfect integrity. The brighter the spot, the stronger the signal (see also description).

Figure 3:
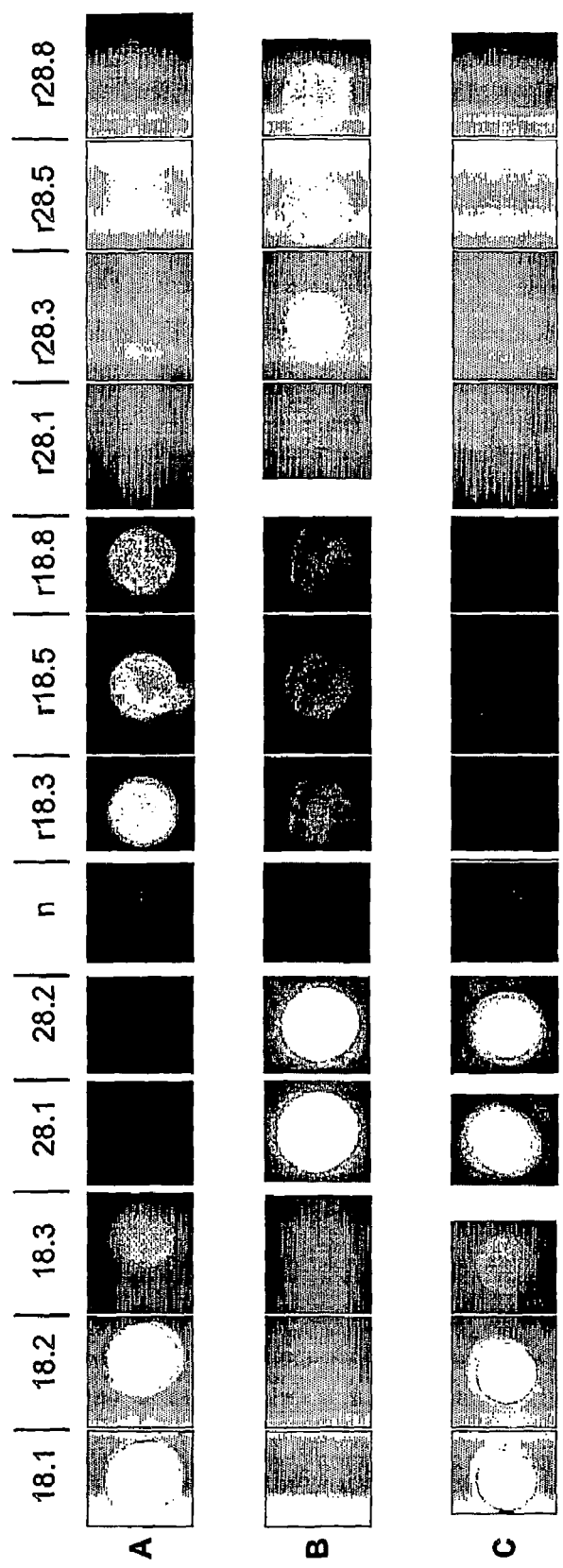

FIG. 3 illustrates the signals obtained in a hybridisation experiment as described in Example 1. Hybridisations were performed on a single support and FIGS. 3A, B and C show the results after hybridisation of the RNA samples and subsequent stacking hybridisation with three oligonucleotide mixtures as explained in Example 1.

Before the subject invention is described further, it is to be understood that the invention is not limited to the particular embodiments of the invention described herein, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

The following examples are offered by way of illustration and not by way of limitation.

EXAMPLES

The following examples of the invention are exemplary and should not be taken as in any way limiting.

Example 1

Detection of rRMA Quality on a Support

This experiment illustrates how rRNA can be detected on a microarray using a 2-step hybridisation. In a first step, sample or target RNA was hybridised to oligonucleotides immobilized on the surface of a solid support. Then in a second step a stacking oligonucleotide, complementary to a different region of the target rRNAs and end-labelled with a fluorescent dye, was hybridised to the rRNA captured on the solid support array.

1.1. Array Design

A solid support (Anopore™, Whatman) was treated with poly-lysine and printed with DNA oligonucleotides designed to capture target rRNA and mRNA by hybridisation. Printed oligonucleotides include control probes and capture probes. A list of the relevant control and capture oligonucleotides used is given in Tables 3 to 6.

1.2. Hybridisation of Sample RNA to the Array of Control and Capture Oligonucleotides Hybridisations were performed for 20 minutes at 42° C. in 5×SSPE buffer with 0.1% (w/v) SDS and 30% formamide using a Multi-Analysis-System (MAS) such as e.g. PamStation 4 and FD10 (PamGene international BV, The Netherlands).

FIGS. 3A and B shows the hybridisation results after contacting the array of printed oligonucleotides (see 1.1.) with a 2 µg aliquot of human total RNA (Human Universal Reference RNA, Strategene). FIG. 1C shows a negative control experiment wherein 100 ng of oligo-dT purified mRNA (Dynabeads) purified from Human Universal Reference RNA was hybridised to the array. This sample represents mRNA present in the total RNA in the absence of non-polyadenylated RNAs including rRNA.

1.3. Hybridisation of Stacking Probes

The hybridised array obtained in 1.2. was washed three times with 20 µl of wash buffer (2 minutes each, 42° C., 5×SSPE). Subsequently, mixes of fluorescent oligonucleotides complementary to one or other rRNA were hybridised to the arrays (20 minutes, 42° C). The stacking probes (Table 7) were Cy3 labelled to allow detection of the rRNA bound to the array. The array was then washed three times (2 minutes each, 42° C., 5×SSPE) and imaged by CCD camera (100 ms exposure) using a BX41 microscope and appropriate filters.

The results as shown in FIG. 3 were obtained after hybridisation of the RNA samples to an array printed with oligonucleotide spots corresponding to SEQ ID Nos 11, 12 and 13 (Table 3); SEQ ID Nos 27 to 29 (Table 5); SEQ ID Nos 19 and 20 (Table 4); and SEQ ID Nos 30-33 (Table 6). The results in FIG. 3A were obtained by a further hybridisation (after the RNA hybridisation) of the stacking oligonucleotides SEQ ID Nos 34-36 (Table 7). The results as shown in FIG. 3B were obtained after stacking hybridisation with a mixture of oligonucleotides corresponding to SEQ ID Nos 37 and 38 (Table 7). The results as shown in FIG. 3C were obtained after a stacking hybridisation with a mixture of oligonucleotides corresponding to SEQ ID Nos 34-38 (Table 7), i.e. a combination of the two sets used in FIGS. 3A and 3B.

1.4. Results and Interpretation

FIG. 3 shows signals corresponding to hybridisations to each relevant unlabelled immobilized oligonucleotide on the array, with Cy3 labelled oligonucleotides complementary to 18S and/or 28S sequences which hybridised either directly to the immobilized oligonucleotides (control spots) or in a "stack" to the sample or target rRNA as an intermediate (hybridised to capture oligonucleotides).

In FIG. 3A, control oligonucleotides 18.1, 18.2 and 18.3 (SEQ ID Nos 11 to 13; Table 3) printed on the array are shown to detect the complementary Cy3-labelled, 18S-specific stacking oligonucleotides by direct DNA:DNA hybridisation. 28S control oligonucleotides 28.1 and 28.2 (SEQ ID Nos 19 and 20; Table 4) were negative as expected, as the Cy3 stacking oligonucleotides were not added to this array. 18S rRNA in the sample is specifically hybridised to oligonucleotide spots r18.3, r18.5 and r18.8 (SEQ ID Nos 27 to 29; Table 5). The average signal from oligonucleotides designed to detect 28S rRNA was <10% of average 18S signal.

In FIG. 3B, control oligonucleotides 28.1 and 28.2 printed on the array are shown to detect the complementary Cy3- labelled 28S-specific stacking oligonucleotides by direct DNA:DNA hybridisation. 18S control oligonucleotides 18.1, 18.2 and 18.3 were negative as expected, as the Cy3 stacking oligonucleotides were not hybridised to the array. 28S rRNA present in the sample is detected by oligonucleotides r28.3, r28.5 and r28.8 (SEQ ID Nos 31 to 33; Table 6). The average signal from 18S-specific oligonucleotides r18.3, r18.5 and r18.8 was <20% of the average 28S signal.

In FIG. 3C, control oligonucleotides 18.1, 18.2, 18.3, 28.1 and 28.2 printed on the array detect the mixture of complementary 18 and 28S Cy3-labelled stacking oligonucleotides by direct DNA:DNA hybridisation. However, those oligonuclmeotides designed to detect rRNA by stacking (r18.3, r18.5, r18.8, r28.1, r28.3, r28.5 and r28.8) give no signal as rRNA is not present.

Example 2 rRNA Quality Assessment and mRNA Transcript Profiling on the Same Array

In the following example the relationship was investigated between rRNA quality on Bioanalyzer or gel and by microarray simultaneously with mRNA transcript profiling on the same array.

In the following example, the relative balance of amplification of mRNA and rRNAs was determined so that both types of amplified RNA give hybridisation signals of appropriate intensity.

In the following example, oligo design can be optimised both for rRNA amplification and also for probe designs printed on the array.

2.1. Microarray Design

A solid array surface (Anopore™, Whatman) is spotted with oligonuclotide sequences using a Packard inkjet printer. The spotted oligonucleotides are between 50 and 65 nucleotides in length and designed against commonly expressed human genes (e.g. beta-actin) using Array Designer software. Oligonucleotides were designed to hybridise to amplified 18S and 28S rRNA as well as commonly used spikes (oligonucleotides designed to hybridise to amplified transcripts/genes not present in human RNA). Oligonucleotide sequences designed to hybridise to amplified rRNA are given in Tables 3 and 5 (18S) and Tables 4 and 6 (28S).

2.2. Co-amplification of mRNA and rRNA

Several amplification and detection methods can be used to amplify or label mRNA and rRNA to facilitate parallel detection by microarray.

2.2.1 Modified Eberwine

In practice, the Van Gelder/Eberwine procedure (U.S. Pat. No. 5,545,522) (using the Ambion Message Amp Kit with the addition of rRNA specific primers) can be used wherein in each case up to 5 μg total RNA samples is primed for reverse transcription with a standard oligo dT primer that adds a T7 RNA polymerase promoter to polyadenylated mRNA (see protocol in the Message Amp Kit). Additionally one primer complementary to the 28S rRNA and another complementary to the 18S rRNA is added to allow amplification of these rRNAs in addition to mRNA. These two sequence-specific primers have a modified T7 promoter to limit amplification of the abundant rRNA molecules, so that the level of rRNA amplification is appropriate when compared to mRNA amplification. Different combinations of primers are used (varying the mutation in the T7 promoter and employing different regions designed to hybridise to rRNA in both the 18S and 28S primer) to ensure an appropriate balance of amplification between the 18 and 28S rRNA primers and the oligo dT mRNA primer. Yield and quality of amplified rRNA is tested spectrophotometrically and by the Agilent Bioanalyzer.

Primer sequences that are used for rRNA amplification are shown in Table 2. Sequences complementary to the rRNA are underlined. The additional sequence required to add the T7 promoter is in bold. It will be noted that in the case of the 18S primers that primer 18T7 has one additional G residue to primer 18T7-G and two compared to primer 18T7-GG. These deletions in 18T7-G and 18T7-GG are a type of mutation known to reduce transcription from this promoter.

2.2.2. Other Labelling Methods

Similarly to the above, other labelling and amplification methods can be performed.

(a) "Tyras", a T7 linear amplification method that transcribes directly on a single-stranded RNA template rather than via a cDNA intermediate. This method also uses the same basic primer designs as in the Eberwine procedure but blocked at the 3' end in accordance with the TYRAS protocol (see Van Gemen, B. European Patent 1 056 884 B1 and U.S. Pat. No. 6,338,954 B1). "Tyras" amplification is performed for both mRNA and rRNA.

(b) Amplification of mRNA as disclosed by Van Gelder/Eberwine in U.S. Pat. No. 5,545,522 and detection of rRNA by hybridisation using fluorescently end-labelled oligo's (e.g. Cy dyes) without amplification. In this case the oligo dT primer amplifying mRNA still has the T7 promoter but the rRNA primers do not. This will either be by:

i. extension of rRNA-specific primer by reverse transcriptase during cDNA synthesis followed by hybridisation of this cDNA to a probe oligo on the array;

ii. unamplified rRNA is hybridised directly to the array, this rRNA is then detected by hybridisation of an additional complementary end-labelled oligo. Oligos may also be labelled by other methods: including dendrimers and other highly-labelled fluorescent particles or structures. Effectively this is a 2-step (or in some cases 3-step, e.g. where the stacking oligonucleotide is itself the target for a fluorescent particle) detection method which is of good specificity but limited sensitivity but. This method can be combined with similar method for the detection of mRNA without amplification or with mRNA amplification methods.

2.2. Hybridisation

Total RNA from three tumour samples (transitional cell carcinoma of the bladder) plus Universal RNA (Stratagene, a high-quality mixture of tumour types) were purified and the 28:18S rRNA ratio assessed using an Agilent Bioanalyser. 2 μg aliquots of the four samples, of varying degrees of degradation as assessed by the rRNA ratios were applied as described in Example 1 to four arrays. After hybridisation the arrays were washed as described in Example 1 to remove unbound material. Subsequently a mixture of 18S and 28S stacking probes was applied to each array and the 28S-specific signal was calculated as the average of the signal from oligonucleotides r28.3, r28.5 and r28.8. The 18S-specific signal was calculated as the average signal from oligonucleotides r18.3, r18.5 and r18.8. The 28S signal was divided by the 18S signal, the results of this experiment are summarised in Table 8.

2.3. Analysis

Hybridisation was quantified by Array Pro 2.0 software from 12 bit raw CCD images. After appropriate processing (background subtraction, normalization to spikes) the signals for each hybridisation reaction were calculated. The normalized signal from array spots were compared with data on rRNA integrity from Agilent Bioanalyzer analysis in order to assess the relationship between the two. In general it is ideal to choose, oligo's for which this relationship is linear allowing them to be good sensors of the 18S and 28S rRNA ratio.

2.4. Interpretation of the Results

The data as shown in Table 8 prove that the stacking method allows monitoring relative abundance of the 28S and 18S rRNAs on a microarray within samples of total RNA purified from human tissue, in this case tumours. The higher quality samples were identified both by the Agilent bioanalyzer and the microarray, and both methods also correctly identified both intermediate and low quality samples. This proves that simultaneous monitoring of rRNA ratio and mRNA levels by microarray analysis is possible as mRNA detection is already routine on microarrays.

The methods according to the present invention allow specific amplification or detection of both 18S and 28S rRNA simultaneously with mRNA amplification and detection by microarray. Methods according to the present invention allow correlating obtained analysis results with the quality of the RNA samples employed and therefore be viable quality control methods.

Example 3

Fine-Tuning the Amplification Procedures

Further experiments can be performed to fine-tune the amplification procedures (including issues of linearity, the choice of mutations in the T7 promoter and issues of hybridisation to rRNA) and refine probe design. In addition, the usefulness of assessing partially degraded rRNA by array can be investigated.

TABLE 1

Promoter mutations known to reduce transcription either by reducing binding of the T7 RNA polymerase or it clearing the promoter region and forming a productive elongation complex.

| SEQ ID No. | Sequence | Mutation |
|---|---|---|
| 1 | TAATACGACTCACTATAGGG | Wild type T7 promoter |
| 2 | TAATACGACTCACTATAGGG | Mutated in initiation region |
| 3 | TAATACGACTCACTATAGGG | Binding region |
| 4 | TAATACGACTCACTATAGGG | TA rich region |
| 5 | TAATACGACTCACTATAGGG | Tolerant of mutations |
| 6 | TAATACGACTCACTATAGGG | Strong downregulation |

TABLE 2

Primer designs for rRNA amplification.

| SEQ ID NO. | Target rRNA | Primer Name | Primer Sequence |
|---|---|---|---|
| 7 | 28S | 28T7 | TAATACGACTCACTATAGGGTTACACGCCGCTCGGTGGAGAAG |
| 8 | 18S | 18T7 | TAATACGACTCACTATAGGGATAGTCAAGTTCGACCGTCTTCTCAG |
| 9 | 18S | 18T7-G | TAATACGACTCACTATAGGATAGTCAAGTTCGACCGTCTTCTCAG |
| 10 | 18S | 18T7-GG | TAATACGACTCACTATAGATAGTCAAGTTCGACCGTCTTCTCAG |

TABLE 3

Oligonucleotide sequences designed to capture amplified 18S RNA where the amplified nucleic acid product is complementary to the original 28S rRNA

| SEQ ID NO. | NO. | Probe Sequence |
|---|---|---|
| 11 | 18.1 | TACCTGGTTGATCCTGCCAGTAGCATATGCTTGTCTCAAAGATTAAGCCATGCATGTCTA |
| 12 | 18.2 | ATCCTGCCAGTAGCATATGCTTGTCTCAAAGATTAAGCCATGCATGTCTAAGTACGCACG |
| 13 | 18.3 | GTACAGTGAAACTGCGAATGGCTCATTAAATCAGTTATGGTTCCTTTGGTCGCTCGCTC |
| 14 | | GGATAACTGTGGTAATTCTAGAGCTAATACATGCCGACGGGCGCTGACCCCCTTCGCGG |
| 15 | | GACGACCCATTCGAACGTCTGCCCTATCAACTTTCGATGGTAGTCGCCGTGCCTACCAT |
| 16 | | GAATCAGGGTTCGATTCCGGAGAGGGAGCCTGAGAAACGGCTACCACATCCAAGGAAGG |
| 17 | | CTTTCGAGGCCCTGTAATTGGAATGAGTCCACTTTAAATCCTTTAACGAGGATCCATTG |
| 18 | | GAGTGTTCAAAGCAGGCCCGAGCCGCCTGGATACCGCAGCTAGGAATAATGGAATAGGA |

TABLE 4

Oligonuoleotide sequences designed to capture amplified 28S RNA where the amplified nucleic acid product is complementary to the original 28S rRNA

| SEQ ID NO. | No. | Probe Sequence |
|---|---|---|
| 19 | 28.1 | GAATTCACCAAGCGTTGGATTGTTCACCCACTAATAGGGAACGTGAGCTGGGTTTAGACC |
| 20 | 28.2 | AGCGTTGGATTGTTCACCCACTAATAGGGAACGTGAGCTGGGTTTAGACCGTCGTGAGAC |
| 21 | | GAGCTGGGTTTAGACCGTCGTGAGACAGGTTAGTTTTACCCTACTGATGATGTGTTGTT |

TABLE 4-continued

Oligonucleotide sequences designed to capture amplified 28S RNA where the amplified nucleic acid product is complementary to the original 28S rRNA

| SEQ ID NO. | No. | Probe Sequence |
|---|---|---|
| 22 | | GGTTTAGACCGTCGTGAGACAGGTTAGTTTTACCCTACTGATGATGTGTTGTTGC |
| 23 | | CTCAGTACGAGAGGAACCGCAGGTTCAGACATTTGGTGTATGTGCTTGGCTGAGG |
| 24 | | CATCTGTGGGATTATGACTGAACGCCTCTAAGTCAGAATCCCGCCCAGGCGAACGATAC |
| 25 | | GAACGTACCATCTGTGGGATTATGACTGAACGCCTCTAAGTCAGAATCCCGCCCA |
| 26 | | CAGCTCCCTCGCTGCGATCTATTGAAAGTCAGCCCTCGACACAAGGGTTTGTCCG |

TABLE 5

Capture oligonucleotides complementary to 18S RNA

| SEQ ID NO. | No. | Probe Sequence |
|---|---|---|
| 27 | r18.3 | GAGCGAGCGACCAAAGGAACCATAACTGATTTAATGAGCCATTCGCAGTTTCACTGTAC |
| 28 | r18.5 | ATGGTAGGCACGGCGACTACCATCGAAAGTTGATAGGGCAGACGTTCGAATGGGTCGTC |
| 29 | r18.8 | TCCTATTCCATTATTCCTAGCTGCGGTATCCAGGCGGCTCGGGCCTGCTTTGAACACTC |

TABLE 6

Capture oligonucleotides complementary to 28S RNA

| SEQ ID NO. | No. | Probe Sequence |
|---|---|---|
| 30 | r28.1 | GGTCTAAACCCAGCTCACGTTCCCTATTAGTGGGTGAACAATCCAACGCTTGGTGAATTC |
| 31 | r28.3 | AACAACACATCATCAGTAGGGTAAAACTAACCTGTCTCACGACGGTCTAAACCCAGCTC |
| 32 | r28.5 | CCTCAGCCAAGCACATACACCAAATGTCTGAACCTGCGGTTCCTCTCGTACTGAG |
| 33 | r28.8 | CGGACAAACCCTTGTGTCGAGGGCTGACTTTCAATAGATCGCAGCGAGGGAGCTG |

TABLE 7

Oligonucleotide sequences of the fluorescently-labelled stacking probes as used in Example 1

| SEQ ID NO. | No. | Target rRNA | Probe Sequence |
|---|---|---|---|
| 34 | 18.3A | 18S | 5' Cy3 - AATGATCCTTCCGCAGGTTCACC |
| 35 | 18.3B | 18S | 5' Cy3 - GATAGTCAAGTTCGACCGTCTTCTCAG |
| 36 | 18.5 | 18S | 5' Cy3 - TTTGAGACAAGCATATGCTACTGGC |
| 37 | 28.3 | 28S | 5' Cy3 - TTACACGCCGCTCGGTGGAGAAG |
| 38 | 28.5 | 28S | 5' Cy3 - TCCCTATTAGTGGGTGAACAATCCA |

TABLE 8

| Sample | 28S:18S ratio (Agilent) | 28S/18S signal (microarray) |
|---|---|---|
| Universal | 2.0 | 0.9 |
| Bladder 1469 | 1.5 | 0.7 |
| Bladder 1473 | 1.4 | 0.7 |
| Bladder 1411 | 1.1 | 0.5 |

The invention claimed is:

1. A method for integrated ribonucleic acid integrity assessment and analysis comprising the steps of:
   (a) providing a support having thereon a set of immobilized detector probes and a set of at least two control probes, wherein
   (i) a first of said at least two control probes is complementary to 23S rRNA or its functional equivalent, or 28S rRNA or its functionally equivalent, and
   (ii) a second of said at least two control probes is complementary to 16S rRNA or its functional equivalent, or 18S rRNA or its functionally equivalent;
   wherein said first and second control probes represent the two major rRNAs of the organism wherefrom a sample is extracted and allow the assessment of integrity of said sample;
   (b) contacting said support with analyte ribonucleic acids derived from a sample, under conditions allowing hybridization of complementary analyte ribonucleic acids and immobilized probes to form analyte ribonucleic acid/probe complexes; wherein said hybridization generates a detectable signal;
   (c) detecting signals generated by said complexes;
   (d) determining the ratio of signals generated by the 28S rRNA/control probe and 18S rRNA/control probe or the 23S rRNA/control probe and 16S rRNA/control probe or functionally equivalent rRNA/control probe complexes;
   (e) assessing the integrity of said sample; and
   (f) evaluating microarray analysis results in view of said integrity assessment.

2. The method according to claim 1, wherein said sample is a total ribonucleic acid sample.

3. The method according to claim 1, wherein said analyte ribonucleic acids are amplified ribonucleic acids.

4. The method according to claim 3, wherein said amplified ribonucleic acids are comprised of amplified ribosomal and messenger ribonucleic acids.

5. The method according to claim 4, wherein said amplified ribosomal ribonucleic acids are comprised of amplified 28S or its functional equivalent and 18S or its functional equivalent, or 23S or its functional equivalent and 16S or its functionally equivalent ribonucleic acids.

6. The method according to claim 3, wherein said amplified analyte ribonucleic acids are labelled.

7. The method according to claim 6, wherein said analyte ribonucleic acids are labelled by means of labelling-by-synthesis.

8. The method according to claim 7, wherein said labelling-by-synthesis comprises the steps of
   (a) providing a total ribonucleic acid sample and contacting said sample with:
      i. a set of ribonucleic acid-specific primers comprising a promoter sequence recognized by an RNA polymerase;
      ii. an enzyme having RNA polymerase activity;
      iii. sufficient amounts of rNTPs;
      wherein either said primers of (i) or said NTPs of (ii) are labelled; and
   (b) maintaining the resulting reaction mixture under the appropriate conditions for a sufficient amount of time for the enzymatic processes to take place.

9. The method according to claim 8, wherein said set of ribonucleic acid-specific primers comprises ribosomal and messenger ribonucleic acid-specific primers.

10. The method according to claim 9, wherein said ribosomal ribonucleic acid-specific primers comprise a mutated promoter sequence; said mutated promoter sequence causing the RNA polymerase to initiate the polymerization reaction less efficiently.

11. The method according to claim 8, wherein said RNA polymerase is chosen from the group including single-subunit phage RNA polymerases, DNA-dependent bacterial RNA polymerases, thermostable RNA polymerases, eukaryotic RNA polymerases and viral RNA polymerases.

12. The method according to claim 8, wherein said RNA polymerase is chosen from the group including T7, SP6 and T3 RNA polymerases.

13. The method according to claim 6, wherein said amplified analyte ribonucleic acids are end-labelled.

14. The method according to claim 6, wherein said amplified analyte ribonucleic acids are fluorescently labelled.

15. The method according to claim 14, wherein said amplified analyte ribonucleic acids are labelled with a fluorescent label chosen from the group including fluorescein, Cy5, and Cy3.

16. The method according to claim 1, wherein said immobilized detector probes are able to hybridize to the amplified messenger ribonucleic acids.

17. The method according to claim 1, which is used for microarray analysis of a ribonucleic acid sample.

18. The method according to claim 1, which is used for simultaneously assessing sample integrity and analysis.

19. The method according to claim 1, which is used for assessing quality of sample ribonucleic acids.

20. The method according to claim 1, which is used for gene expression analysis.

* * * * *